United States Patent [19]

Sparks et al.

[11] Patent Number: 4,940,588

[45] Date of Patent: Jul. 10, 1990

[54] CONTROLLED RELEASE POWDER AND PROCESS FOR ITS PREPARATION

[75] Inventors: Randall T. Sparks, Gainesville, Ga.; Edward J. Geoghegan, Athlone, Ireland

[73] Assignee: Elan Corporation, Athlone, Ireland

[21] Appl. No.: 171,131

[22] Filed: Mar. 17, 1988

Related U.S. Application Data

[63] Continuation of Ser. No. 792,801, Oct. 30, 1985, abandoned.

[30] Foreign Application Priority Data

Oct. 30, 1984 [IE] Ireland .................................. 2788/84

[51] Int. Cl.$^5$ ........................... A61K 9/14; A61K 9/16
[52] U.S. Cl. ........................................ 424/490; 424/48; 424/440; 424/441; 424/464; 424/469; 424/470; 424/484; 424/486; 424/487; 424/488; 424/489; 424/494; 424/497
[58] Field of Search .................. 424/48, 440, 441, 464, 424/469, 470, 484, 486, 487, 488, 489, 490, 494, 497

[56] References Cited

U.S. PATENT DOCUMENTS

| | | | |
|---|---|---|---|
| 2,928,770 | 3/1960 | Bardani | 167/82 |
| 3,115,441 | 12/1963 | Hermelin | 167/82 |
| 3,341,416 | 9/1967 | Anderson et al. | 167/83 |
| 3,432,593 | 3/1969 | Shepard | 424/20 |
| 3,460,972 | 8/1969 | Nack | 427/213.3 X |
| 3,488,418 | 1/1970 | Holliday et al. | 424/35 |
| 3,520,970 | 7/1970 | Lehmann | 424/25 |
| 3,539,465 | 11/1970 | Hiestand | 252/316 |
| 3,567,650 | 3/1971 | Bakan | 252/316 |
| 3,576,759 | 4/1971 | Powell et al. | 252/316 |
| 3,594,326 | 7/1971 | Himmel | 252/316 |
| 3,594,470 | 7/1971 | Borodkin et al. | 424/32 |
| 3,629,392 | 12/1971 | Banker et al. | 424/487 X |
| 3,629,392 | 12/1971 | Banker et al. | 424/22 |
| 3,634,586 | 1/1972 | Kaser et al. | 424/80 |
| 3,639,306 | 2/1972 | Sternberg et al. | 260/2.5 B |
| 3,642,978 | 2/1972 | Ogawa et al. | 424/37 |
| 3,657,144 | 4/1972 | Yoshida | 252/316 |
| 3,691,090 | 9/1972 | Kitajima et al. | 252/316 |
| 3,703,576 | 11/1972 | Kitajima et al. | 424/35 |
| 3,714,065 | 1/1973 | Kitajima et al. | 252/316 |

(List continued on next page.)

FOREIGN PATENT DOCUMENTS

| | | |
|---|---|---|
| 873815 | 6/1971 | Canada . |
| 1025359 | 5/1973 | Canada .................. 167/164 |
| 1142810 | 3/1983 | Canada .................. 117/45.2 |
| 0002574 | 1/1978 | European Pat. Off. . |
| 0094513 | 4/1983 | European Pat. Off. . |
| 8300284 | 7/1982 | PCT Int'l Appl. . |
| 1056259 | 1/1967 | United Kingdom . |
| 1205769 | 9/1970 | United Kingdom . |
| 1287431 | 8/1972 | United Kingdom . |
| 1478947 | 7/1977 | United Kingdom . |
| 1569036 | 6/1980 | United Kingdom . |
| 2059764 | 9/1980 | United Kingdom . |
| 2017624B | 7/1982 | United Kingdom . |
| 2147501A | 9/1985 | United Kingdom . |

OTHER PUBLICATIONS

Beck et al., "A New Long-Acting Injectable Microcapsule System . . . ", *Fertility and Sterility*, vol. 31, No. 5, May 1979, pp. 545-551.

Fong et al., "Evaluation of Biodegradable Microspheres Prepared by a Solvent Evaporation Process . . . ", *J. of Controlled Release*, 3 (1986), 119-130.

*Primary Examiner*—Shep K. Rose
*Attorney, Agent, or Firm*—Robert H. Falk; Henry Croskell

[57] ABSTRACT

A controlled release powder containing discrete microparticles for use in edible, pharmaceutical and other controlled release compositions is disclosed. The microparticles have an average size in the range of from 0.1 to 125 μm. Each of the micro-particles is in the form of a micromatrix of an active ingredient uniformly distributed in at least one non-toxic polymer. The micro-particles have a predetermined release of active ingredient when the dissolution rate thereof is measured according to the Paddle Method of U.S. Pharmacopoeia XX at 37° C. and 75 r.p.m.

7 Claims, 15 Drawing Sheets

U.S. PATENT DOCUMENTS

| | | | |
|---|---|---|---|
| 3,725,556 | 4/1973 | Hanssen et al. | 424/357 |
| 3,728,445 | 4/1973 | Bardani | 424/22 |
| 3,732,172 | 5/1973 | Herbig et al. | 252/316 |
| 3,737,337 | 6/1973 | Schnoring et al. | 427/213.3 X |
| 3,775,537 | 11/1973 | Lehmann | 424/21 |
| 3,780,195 | 12/1973 | Balassa | 426/350 |
| 3,821,422 | 6/1974 | Morse et al. | 426/72 |
| 3,835,221 | 9/1974 | Fulberth et al. | 424/20 |
| 3,859,228 | 1/1975 | Morishita et al. | 252/316 |
| 3,860,733 | 1/1975 | Morse et al. | 426/302 |
| 3,887,699 | 6/1975 | Yolles | 424/19 |
| 3,891,570 | 6/1975 | Fukushima et al. | 252/316 |
| 3,909,444 | 9/1975 | Anderson et al. | 424/488 X |
| 3,909,444 | 9/1975 | Anderson et al. | 252/316 |
| 3,922,338 | 11/1975 | Estevenel et al. | 424/21 |
| 3,943,063 | 3/1976 | Morishita et al. | 427/213.36 |
| 3,951,851 | 4/1976 | Kitajima et al. | 252/316 |
| 3,954,959 | 5/1976 | Pederson | 424/21 |
| 3,959,457 | 5/1976 | Speaker et al. | 424/19 |
| 4,011,312 | 3/1977 | Reuter et al. | 424/78 |
| 4,016,254 | 4/1977 | Seager | 424/33 |
| 4,083,949 | 4/1978 | Benedikt | 424/19 |
| 4,101,651 | 7/1978 | Kobayashi et al. | 424/35 |
| 4,118,336 | 10/1978 | Morishita et al. | 252/316 |
| 4,123,381 | 10/1978 | Morishita et al. | 252/316 |
| 4,182,778 | 1/1980 | Hall et al. | 426/72 |
| 4,201,822 | 5/1980 | Cowsar | 428/240 |
| 4,205,060 | 5/1980 | Monsimer et al. | 424/14 |
| 4,221,862 | 9/1980 | Naito et al. | 430/530 |
| 4,223,006 | 9/1980 | Taskis | 424/16 |
| 4,230,687 | 10/1980 | Sair et al. | 424/488 X |
| 4,230,687 | 10/1980 | Sair et al. | 424/22 |
| 4,254,100 | 3/1981 | Keller et al. | 424/37 |
| 4,293,539 | 10/1981 | Ludwig et al. | 424/19 |
| 4,321,253 | 3/1982 | Beatty | 424/35 |
| 4,324,683 | 4/1982 | Lim et al. | 252/316 |
| 4,368,197 | 1/1983 | Shefter | 514/186 |
| 4,384,975 | 5/1983 | Fong | 427/213.36 |
| 4,389,330 | 6/1983 | Tice et al. | 427/213.36 |
| 4,415,547 | 11/1983 | Yu et al. | 424/19 |
| 4,452,821 | 6/1984 | Gergely | 424/48 |
| 4,489,055 | 12/1984 | Couvreur et al. | 424/487 X |
| 4,489,055 | 12/1984 | Couvreur et al. | 424/7.1 |
| 4,497,832 | 2/1985 | Cherukuri et al. | 426/5 |
| 4,587,118 | 5/1986 | Hsiao | 424/19 |
| 4,605,550 | 8/1986 | Trill | 424/487 |
| 4,605,550 | 8/1986 | Trill | 424/22 |
| 4,632,822 | 12/1986 | Peters et al. | 424/155 |
| 4,647,450 | 3/1987 | Peters et al. | 424/48 |
| 4,647,459 | 3/1987 | Peters et al. | 424/155 |
| 4,678,516 | 7/1987 | Alderman et al. | 424/488 X |
| 4,678,516 | 7/1987 | Alderman et al. | 106/197.1 |
| 4,690,682 | 9/1987 | Lim | 424/499 |
| 4,690,825 | 9/1987 | Won | 424/501 |
| 4,690,825 | 9/1987 | Won | 424/501 |
| 4,749,575 | 6/1988 | Rotman | 424/441 |
| 4,789,516 | 12/1988 | Lim | 424/499 |
| 4,800,087 | 1/1989 | Mehta | 424/497 |
| 4,818,542 | 4/1989 | DeLuca et al. | 424/491 |
| 4,818,542 | 4/1989 | DeLuca et al. | |

CONTROLLED RELEASE POWDER AND PROCESS FOR ITS PREPARATION

RELATED APPLICATIONS

This application is a continuation of Ser. No. 792,801 filed 10.30.85 now abandoned

BACKGROUND OF THE INVENTION

This invention relates to controlled release formulations and, in particular, to sustained release powders consisting of discrete micro-particles.

Many types of controlled or sustained release pellets are known which are loaded into capsules for oral administration. These pellets can be described as macro-particles and invariably have an average size greater than 400 μm.

Sustained release pellets cannot be readily formulated as liquids. Sustained release liquids are desirable for use as geriatric and pediatric formulations.

Various processes are known for the production of micro-spheres using solvent evaporation emulsion techniques. Known micro-encapsulation techniques are generally employed for phase transformation, such as for the conversion of liquids to solids. Alternatively, such techniques may be used for protecting an active material, such as coating aspirin to mask its stomach irritant properties.

Sustained release liquids are known which contain ion exchange resins. In such sustained release liquids the active ingredient is bound to an ion exchange resin in the form of a reversible complex and is displaced therefrom in vivo. Such sustained release liquids are described, for example, in French Patent Publication No. 2 278 325.

SUMMARY OF THE INVENTION

It is an object of the present invention to provide a controlled release powder of discrete micro-particles which can be readily formulated in liquid form but which can also be formulated in other sustained release forms such as tablets which have improved properties relative to the known forms.

It is another object of the present invention to provide a process for preparing the controlled release powder of the present invention. This process comprises:
(a) forming a solution of a polymer or polymers in a solvent;
(b) dissolving or dispersing an active ingredient in the polymer solution to form an uniform mixture; and
(c) removing the solvent from the mixture to obtain micro-particles having an average size of from 0.1 to 125 μm.

It is another object of the present invention to provide controlled release antibiotic formulations substantially free from the taste of the antibiotic for pharmaceutical or veterinary use. These controlled release antibiotic formulations are in the form of powders, non-aqueous suspensions of powders, or reconstitutable aqueous suspensions of powders according to the present invention.

BRIEF DESCRIPTION OF THE DRAWINGS

In describing the present invention, reference will be made to the accompanying drawings in which.

DETAILED DESCRIPTION OF THE PREFERRED EMBODIMENTS

Figure 1:
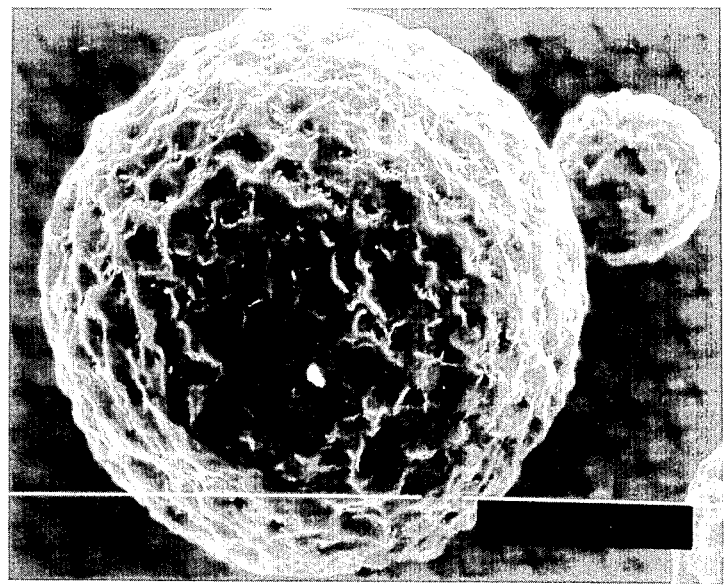
FIG. 1 is a half-tone drawing prepared from an electron micrograph of "pharmasomes" of the present invention containing theophylline.

The present invention provides a controlled release powder containing discrete micro-particles for use in edible, pharmaceutical and other sustained release compositions. The powder of the present invention comprises particles containing an active ingredient and optionally an excipient in intimate admixture with at least one non-toxic polymer, each of the particles is in the form of a micromatrix with the active ingredient and the excipient, if present, uniformly distributed throughout the polymer. The particles have an average size of from 0.1 to 125 μm and have a predetermined release of active ingredient. The dissolution rate thereof can be measured according to the Paddle Method of U.S. Pharmacopoeia XX at 37° C. and 75 r.p.m. Preferably, the particles have an average size of from 5 to 100 μm.

The term "pharmasomes" has been coined for the micro-particles of the powder according to the present invention and this term is used hereinafter to refer to the micro-particles of the powder.

The controlled release powders according to the invention can permit a sustained release of active ingredient as hereinafter demonstrated.

The active ingredient, preferably, is a drug, a nutrient, a coloring agent, a fragrance, a herbicide, a pesticide, a flavoring agent or a sweetening agent.

The powder can be dispersed or suspended in a liquid vehicle and will maintain its sustained release characteristics for a useful period of time. These dispersions or suspensions have both chemical stability and stability in terms of dissolution rate.

The polymer may be soluble, insoluble, permeable, impermeable or biodegradable. The polymers may be polymers or copolymers. The polymer may be a natural or synthetic polymer. Natural polymers include polypeptides, polysaccharides and alginic acid. A suitable polypeptide is zein and a suitable polysaccharide is cellulose.

Representative synthetic polymers include alkyl celluloses, hydroxyalkyl celluloses, cellulose ethers, cellulose esters, nitro celluloses, polymers of acrylic and methacrylic acids and esters thereof, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes and polyurethanes and co-polymers thereof. The polymer to be used is governed by its toxicity and its compatibility with the particular active ingredient being used and can be selected without difficulty by those skilled in the art.

Particularly suitable polymers include: methyl cellulose, ethyl cellulose, hydroxypropyl cellulose, hydroxypropyl methyl cellulose, hydroxybutyl methyl cellulose, cellulose acetate, cellulose propionate (lower, medium or higher molecular weight), cellulose acetate propionate, cellulose acetate butyrate, cellulose acetate phthalate, carboxymethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene glycol), poly(ethylene oxide), poly(ethylene terephthalate), poly(vinyl alcohol), poly(vinyl isobutyl ether), poly(vinyl acetate), poly(vinyl chloride) and polyvinylpyrrolidone.

Especially suitable co-polymers include: butyl methacrylate/isobutyl methacrylate co-polymer, high molecular weight, methylvinyl ether/maleic acid co-polymer, methylvinyl ether/maleic acid, monoethyl ester co-polymer, methylvinyl ether/maleic anhydride co-polymer and vinyl alcohol/vinyl acetate co-polymer.

Representative biodegradable polymers include, polylactides, polyglycolides, poly(ethylene terephthalate) and polyurethane.

Representative acrylates and methacrylates are polyacrylic and methacrylic polymers such as those sold under the Trade Mark Eudragit.

When the active ingredient is a drug there is essentially no limitation on the type of drug which may be used.

Representative active ingredients include antacids, anti-inflammatory substances, coronary dilators, cerebral dilators, peripheral vasodilators, anti-infectives, psychotropics, anti-manics, stimulants, anti-histamines, laxatives, decongestants, vitamins, gastro-intestinal sedatives, anti-diarrheal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics and anti-uricemic drugs.

Typical active ingredients include gastro-intestinal sedatives such as metoclopramide and propantheline bromide; antacids such as aluminium trisilicate, aluminium hydroxide and cimetidine; anti-inflammatory drugs such as phenylbutazone, indomethacin, naproxen, ibuprofen, flurbiprofen, diclofenac, dexamethasone, prednisone and prednisolone; coronary vasodilator drugs such as glyceryl trinitrate, isosorbide dinitrate and pentaerythritol tetranitrate; peripheral and cerebral vasodilators such as soloctidilum, vincamine, naftidrofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine; central nervous stimulants such as methylphenidate, ephedrine, epinephrine, isoproterenol, amphetamine sulfate and amphetamine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfosuccinate; nutritional supplements such as ascorbic acid, alpha tocopherol, thiamine and pyridoxine; anti-spasmodic drugs such as dicyclomine and diphenoxylate; drugs affecting the rhythm of the heart such as verapamil, nifedipine, diltiazem, procainamide, disopyramide, bretylium tosylate, quinidine sulfate and quinidine gluconate; drugs used in the treatment of hypertension such as propranolol hydrochloride, guanethidine monosulphate, methyldopa, oxprenolol hydrochloride, captopril and hydralazine; drugs used in the treatment of migraine such as ergotamine; drugs affecting coagulability of blood such as epsilon aminocaproic acid and protamine sulfate; analgesic drugs such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenamic acid; anti-epileptic drugs such as phenytoin sodium and sodium valproate; neuromuscular drugs such as dantrolene sodium; substances used in the treatment of diabetes such as tolbutamide, disbenase glucagon and insulin; drugs used in the treatment of thyroid gland disfunction such as triiodothyronine, thyroxine and propylthiouracil, diuretic drugs such as furosemide, chlorthalidone, hydrochlorthiazide, spironolactone and triamterene; the uterine relaxant drug ritodrine; appetite suppressants such as fenfluramine hydrochloride, phentermine and diethylproprion hydrochloride; anti-asthmatic and bronchodilator drugs such as aminophylline, theophylline, salbutamol, orciprenaline sulphate and terbutaline sulphate; expectorant drugs such as guaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; haemopoietic drugs such as ferrous sulphate, folic acid and calcium gluconate; uricosuric drugs such as sulphinpyrazone, allopurinol and probenecid.

Particularly preferred active ingredients are: ibuprofen, acetaminophen, 5-amino-salicylic acid, dextromethorphan, propranolol, theophylline, diltiazem, methyldopa, pseudoephedrine, cimetidine, cephalexin, cephaclor, cephradine, naproxen, piroxicam, diazepam, diclofenac, indomethacin, amoxycillin, pivampicillin, bacampicillin, dicloxacillin, erythromycin, erythromycin stearate, lincomycin, co-dergocrine mesylate, doxycycline, dipyridamole, frusemide, triamterene, sulindac, nifedipine, atenolol, lorazepam, glibenclamide, salbutamol, trimethoprim/sulphamethoxazole, spironolactone, carbinoxamine maleate, guaiphenesin, potassium chloride and metoprolol tartrate.

Especially preferred active ingredients include theophylline, acetaminophen and potasium chloride.

The active ingredient may also be a saccharin for use in edible compositions wherein it is desired to obtain a controlled release of saccharin, such as, for example in chewing gums. The active ingredient may also be other sweetening agents, such as, for example, aspartame which is especially suitable for use in chewing gums.

The present invention also provides a process for preparing the controlled release powder according to the invention which comprises:
  (a) forming a solution of the polymer or polymers in a solvent;
  (b) dissolving or dispersing the active ingredient in said polymer solution to form an uniform mixture; and
  (c) removing the solvent from the mixture to obtain micro-particles having an average size of from 0.1 to 125 μm.

The particles obtained, preferably, have an average size of from 5 to 100 μm.

The solvent is selected from water, alcohols, ketones, halogenated aliphatic compounds, halogenated aromatic hydrocarbon compounds, aromatic hydrocarbon compounds and cyclic ethers or a mixture thereof.

Especially preferred solvents include, water, hexane, heptane, methanol, ethanol, acetone, methylethyl ketone, methylisobutyl ketone, methylene chloride, chloroform, carbon tetrachloride, toluene, xylene and tetrahydrofuran.

The choice of solvent or solvents will be dictated by the particular polymer or polymers selected and can be chosen without difficulty by those skilled in the art. For example, suitable solvents for use with the celluloses are acetone or a mixture of methanol and methylene chloride.

The concentration of the polymer in the solvent will normally be less than 75% by weight. Normally the concentration will be in the range of 10-30% by weight.

If the active ingredient is not soluble in the polymer solution the particle size of the active ingredient is reduced to less than 10 μm. The reduction of particle size may be achieved by milling, for example, by ball milling or jet milling.

The active ingredient may, of course, be a liquid.

The ratio of drug to polymer will vary within wide limits, such as within the range of from 0.1:10 to 10:1.

The uniform mixture of the active ingredient in the polymer solution may be achieved by rapid and continuous mixing.

The removal of the solvent and the formation of particles of the desired size may be achieved in a number of ways as described below.

1. SPRAY DRYING.

The mixture of active ingredient and polymer in the solvent is sprayed into a stream of hot air in a conventional manner. This causes the solvent to evaporate and the powder is collected in the spray drying vessel.

The size of the particles may be controlled in a number of ways, for example, by pre-selecting the inlet and outlet temperature of the spray drying vessel; the rate of introduction of the spray, the size of the spray tip or the ratio of the concentration of active ingredient to polymer.

2. USE OF AN EXTERNAL LIQUID PHASE.

The mixture of active ingredient and polymer, which is in the form of a solution or suspension, is poured into a liquid external phase. The liquid external phase comprises a solvent which is immiscible or partially immiscible with the active ingredient/polymer mixture.

The choice of external liquid phase will be determined by the particular combination of active ingredient and polymer selected. Suitable liquids for the external liquid phase include water, aqueous solutions, for example, sugar solutions, organic solvents, mineral oil, vegetable oils, fixed oils, syrups or silicones. The aqueous solution may include a thickening agent, such as xanthan gum, to increase the viscosity thereof. Oils may be made more viscous by the addition of substances such as magnesium stearate. The external liquid phase may also comprise a solution of a different pH, for example, a buffer.

The ratio of external liquid phase to polymer mixture will be at least 2:1.

Following addition of the active ingredient/polymer mixture to the external liquid phase, the two phase mixture obtained is emulsified, for example, by rapid mixing. The emulsion formed may be either stable or unstable. Globules of the active ingredient/polymer are thereby formed in the emulsion.

The solvent may be removed in a number of ways. If the solvent is volatile it can be removed passively. For example, if the solvent is acetone it would normally be removed by evaporation during the mixing step. The particles formed are then harvested by filtration or centrifugation.

The solvent can also be removed by heating while mixing the two phase mixture. For example, the solvent may be removed on a rotary film evaporator. The solvent may also be removed under vacuum with or without heating. Microwave drying may also be employed with or without the application of a vacuum. Another mode of solvent removal is freeze drying.

After harvesting of the micro-particles, they will normally be given successive washings with a suitable solvent, followed by drying. For example, when the solvent used is acetone and the external liquid phase is mineral oil, the micro-particles will be successively washed with hexane and then dried at 45° C.

On a commercial scale emulsification of the mixture may be achieved by emulsification with an in-line mixer or mixers.

The particle size may be controlled in a number of ways. For example, the particle size may be controlled by the rate of mixing, the viscosity of the external liquid phase, the viscosity of the internal phase, the active ingredient particle size or the volatility of the solvent.

3. Other methods for the removal of the solvent include phase separation, interfacial polymer deposition and coacervation.

The optional excipient used in association with the active ingredient will frequently have an active role to play following administration. For example, the excipient may be a surface-active agent which facilitates the transport of water into the particles, for example, sodium lauryl sulphate or a polyoxyethylene sorbitan ester such as that sold under the Trade Mark Tween a product of ICI America, Atlas Division. The excipient may also be an active transport agent such as, for example, glucose or one or more amino acids.

The excipient may comprise one or more organic acids which facilitate the dissolution of drugs which are poorly soluble in alkaline media. Such acids include, for example, ascorbic acid, citric acid, fumaric acid, malic acid, succinic acid and tartaric acid. Similarly, the excipient may comprise one or more basic materials which facilitate the dissolution of drugs which are poorly soluble in acid media. Such basic materials include sodium carbonate, sodium citrate and sodium bicarbonate.

When the active ingredient is a drug, the micro-particles according to the invention may be formulated in a wide variety of forms. Pharmaceutical formulations according to the invention include pills and tablets, for example, coated tablets, effervescent tablets, chewable tablets, molded tablets and melt tablets. The particles according to the invention may be compressed into tablets and optionally coated without any substantial change occurring in the particles. Furthermore, because of the micro-particulate nature of the particles they are unlikely to be significantly degraded or ground by any chewing action.

Powder formulations according to the invention include dusting powders and douche powders.

The particles according to the invention may also be loaded into capsules which may be either soft gelatin capsules or hard gelatin capsules.

Other solid dosage forms include pessaries, rectal suppositories, vaginal tablets and vaginal inserts.

The particles according to the invention may also be used in implants and ocular inserts.

The powders can also be formulated in forms suitable for topical application, such as, for example, creams or ointments and for transdermal delivery, for example, in the form of transdermal patches.

The micro-particulate powders according to the invention may also be used in the form of foams, gels, pastes, gums, mucilages and jellies.

Other suitable formulations incorporating the micro-particles according to the invention include inhalants, magmas, intrauterine devices, patches, biodegradable wound dressings and other topical dressings.

The micro-particulate powders according to the invention are especially suitable for formulation as liquids for oral, local or parenteral administration. Thus, they can be formulated in liquid form for use as eye drops, nasal drops, ear drops, suspensions, syrups, infusion and injectable solutions. The powders can also be formulated as nasal sprays. The injectable solutions include intravenous, subcutaneous and intramuscular injectable solutions.

The oral suspensions and syrups according to the invention are particularly suitable for use in geriatric and pediatric medicine. The liquids formed have good mouth feel. Furthermore, because the polymer substantially coats the active ingredient, the coating masks any unpleasant taste.

A characteristic of good mouth feel also applies to chewable and effervescent tablets. Because of the micro-particulate nature of the powder one does not experience a granular sensation.

Preferred pediatric liquids according to the invention are suspensions or syrups of bronchial relaxants, analgesics, anti-pyretics, anti-tussives, anti-spasmodics, anti-nauseants, anti-histamines, anti-epileptics and antibiotics.

Other especially suitable liquid formulations according to the invention are non-aqueous suspensions of highly water soluble or water insoluble active ingredients. Suitable drugs for these formulations include dextromethorphan, guaiphenesin and pseudoephedrine or a salt thereof or potassium chloride.

The liquid formulations have good shelf life and demonstrate chemical stability and stability in terms of dissolution rate for up to six months. It is estimated that the shelf life can be as long as five years.

In the liquid formulations according to the invention a concentration of active ingredient of up to 1 g per 5 ml can be achieved.

Heretofore many drugs have not been stable in liquid form, for example, analgesics, necessitating a dosage regimen of every 4–6 hours. The liquids according to the invention offer versatility and the possibility of twice daily administration for a medicament such as, for example, analgesics, anti-histamines and bronchial relaxants.

The taste masking feature of the powders according to the invention is of significant importance in the area of pediatric medicine. However, this feature is of equal importance in veterinary medicine. For example, in the case of antibiotics such as erythromycin which have an extremely unpleasant bitter taste it is virtually impossible to administer such antibiotics orally to animals because it is not possible to successfully mask the bitter taste. Accordingly, such known oral formulations are rejected by animals.

The present invention therefore in one important aspect provides controlled release antibiotic formulations substantially free from the taste of said antibiotic for pharmaceutical or veterinary use which:
  (a) are in the form of powders according to the invention;

(b) are in the form of non-aqueous suspensions of the powders according to the invention; or (c) are in the form of reconstitutable aqueous suspensions of the powders according to the invention.

The powders according to the invention can be used in pre-mixes for animal feedstuffs and other feed additives.

In addition to drugs, nutritional supplements such as vitamins can be administered orally to animals using the powders according to the invention.

Suitable veterinary preparations according to the invention include veterinary feeds, boluses, drenches and washes.

In the agricultural field the powders according to the invention can also be used for preparation of controlled release herbicides and pesticides.

In the cosmetics field one use of the controlled release powders according to the invention is as sustained release fragrance particles for use in talcum powders, creams, lotions and other cosmetic preparations.

Figure 2:
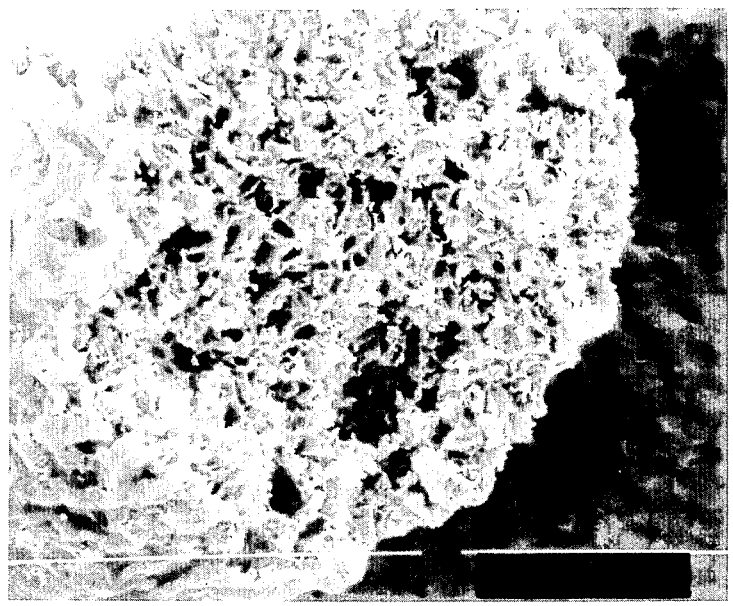
FIG. 2 is a half-tone drawing prepared from an electron micrograph of "pharmasomes" of the present invention containing theophylline after theophylline has been leached out by dissolution in water for 24 hours.

Each of the particles of the controlled release powder according to the invention represents a true micromatrix with the active ingredient and optionally one or more excipients uniformly distributed therethrough as depicted in FIG. 1 of the accompanying drawings which is a half-tone drawing prepared from an electron micrograph of "pharmasomes" containing theophylline and prepared as described in Example 1 below. The theophylline can be observed to form veins or a labyrinth throughout the polymeric material of the "pharmasomes". FIG. 2 is a half-tone drawing prepared from an electron micrograph of the "pharmasomes" after the theophylline has been leached out by dissolution in water for 24 hours. It may be observed that a matrix structure of polymeric materials remains.

The micromatrix nature of the particles can also be demonstrated by their dissolution profile. Referring, for example, to Examples 1 and 2 hereinbelow, it is found that the dissolution rate (D) is directly proportional to the square root of time (t), after an initial burst of release of active ingredient, according to the following equation:

$$D = a\sqrt{t}$$

The initial burst of release of active ingredient is considered to be active ingredient lying close to the surface of the particles. The dissolution rate is dependent on the amount of active ingredient remaining in the particle matrix at any given time. Theoretically the last molecule of active ingredient never leaches out. The dissolution rate is assumed to reach 100% at infinity.

The particles according to the invention also have a degree of porosity which can be calculated from the absolute density of the particles measured on a pycnometer. The dissolution rate of the particles according to the invention is also found to relate to the degree of porosity of said particles.

The microparticles according to the invention are to be distinguished from microcapsules in that in the latter the active ingredient is encapsulated by a polymer coating, whereas in the former the active ingredient is uniformly distributed throughout the polymeric material as described above and as illustrated in FIGS. 1 and 2 of the accompanying drawings.

The invention will now be further illustrated by the following examples. The following examples are intended to be merely illustrative of the present invention and are not intended to be limiting in any way. In the following examples the dissolution rate of the various pharmaceutical formulations is measured by the Paddle Method of U.S. Pharmacopoeia XX at 37° C. and 75 r.p.m., using 200 mg of sample per 900 ml of simulated intestinal fluid excluding enzymes.

EXAMPLE 1

Preparation of micro-particles containing theophylline

Theophylline was ground in a motorized ball mill and then sieved through a 38 μm mesh sieve.

Cellulose acetate butyrate (CAB) was dissolved in acetone to give a concentration of CAB in acetone of 15% w/v.

Hexane (20 ml) was added to an aliquot of the CAB solution (100 g) with constant stirring.

A portion of the sieved theophylline (10 g) was then added to the polymer solution under constant agitation to ensure an even dispersion of the theophylline. This product constituted an internal phase for the subsequent emulsification step.

Magnesium stearate was dissolved in heavy mineral oil U.S. Pharmacopoeia so as to achieve a concentration of 1.5% w/v. This solution was used as an external liquid phase. 150 ml of the external liquid phase was decanted into a tall 600 ml beaker and the internal phase prepared above was added thereto. Emulsification was achieved using a Silverson ™ L-2R mixer, a lab-scale homgenizer, at full speed (6,000 r.p.m.) for 2 minutes and then dropping the speed as required to achieve the desired particle size.

The suspension of particles in the external phase was then introduced into a rotary evaporator and the acetone was removed under vacuum. The suspension now consisted solely of polymer coated theophylline or "pharmasomes" suspended in the external liquid phase. On microscopic examination the particle size of the "pharmasomes" was found to range from 10 to 180 μm.

The particles were centrifuged at 2500 r.p.m. for five minutes and the external phase was decanted. The particles were then washed four times with 100 ml of heptane to remove the external liquid phase. The final product was then filtered over Whalton #4 filter paper and dried at 45° C. for two hours. The particles were then sieved with mesh sizes of 50, 90, 125 and 180 μm sieve.

The dissolution rate of the 90–125 μm fraction of the particles was estimated using the Paddle Method of U.S. Pharmacopoeia XX as indicated above. The results were as follows:

| Time (h) | % Release |
| --- | --- |
| 0.5 | 42 |
| 1 | 57 |
| 2 | 62 |
| 3 | 65 |
| 4 | 69 |
| 5 | 73 |
| 6 | 78 |
| 7 | 85 |
| 8 | 91 |
| 9 | 95 |
| 10 | 97 |

The particles were found to be tasteless with complete masking of the mormally bitter taste of theophylline.

EXAMPLE 2

Preparation of micro-particles containing acetaminophen

Example 1 was repeated except that 20 g of acetaminophen was used in place of 10 g of theophylline. In the external liquid phase heavy mineral oil was replaced by light mineral oil. A major proportion of the particles had an average size of 90 μm.

The dissolution rate of the particles was determined and was found to be as follows:

| Time (h) | % Release |
| --- | --- |
| 0 | 0 |
| 0.5 | 43 |
| 1 | 55 |
| 2 | 67 |
| 3 | 75 |
| 4 | 80 |
| 5 | 85 |
| 6 | 89 |
| 7 | 91 |
| 8 | 96 |

The particles were found to be tasteless.

EXAMPLE 3

Preparation of micro-particles containing nifedipine

Example 1 was repeated except that 16 g of nifedipine was used in place of theophylline. The internal phase consisted of Eudragit RS 100 ™ (a product of Rohm and Haas) in methanol at a concentration of 33% w/v. The external phase consisted of magnesium stearate in light mineral oil at a concentration of 2.5% w/v.

The dissolution rate of the particles formed was determined and was found to be as follows:

| Time (h) | % Release |
| --- | --- |
| 0.5 | 25 |
| 1 | 30 |
| 2 | 35 |
| 3 | 55 |
| 4 | 70 |
| 6 | 85 |

The particles were tasteless.

EXAMPLE 4

Preparation of micro-particles containing dextromethorphan hydrobromide

Example 1 was repeated except that 10 g of theophylline was replaced by 10 g of dextromethorphan hydrobromide.

The dissolution rate of the particles was determined and was found to be as follows:

| Time (h) | % Release |
| --- | --- |
| 0.5 | 45 |
| 1 | 55 |
| 2 | 70 |
| 3 | 74 |
| 4 | 80 |
| 5 | — |
| 6 | 90 |

EXAMPLE 5

Preparation of micro-particles containing saccharin sodium

Example 1 was repeated except that theophylline was replaced by 6.5 g of saccharin sodium. The internal phase consisted of Ethocel ™ (Dow Corning's trademarked ethyl cellulose product) 45 cps dissolved in ethanol to give a concentration of 15% w/v. Saccharin sodium was added to 50 g of the polymer solution. The external liquid phase consisted of heavy mineral oil U.S. Pharmacopoeia.

The dissolution rate of the particles was determined and was found to be as follows:

| Time (min) | % Release |
| --- | --- |
| 5 | 60 |
| 10 | 75 |
| 15 | 89 |
| 30 | 94 |
| 60 | 100 |

EXAMPLE 6

Preparation of micro-particles containing pseudoephedrine hydrochloride

The procedure of Example 1 was repeated except that theophylline was replaced by 10 g of pseudoephedrine hydrochloride. 50 g of CAB was used which was dissolved in 20 ml of hexane to form the polymer solution.

The dissolution rate of the particles was determined and found to be as follows:

| Time (h) | % Release |
| --- | --- |
| 0.5 | 35 |
| 1 | 55 |
| 2 | 60 |
| 3 | 68 |
| 4 | 73 |
| 5 | 80 |
| 6 | 84 |
| 7 | 90 |
| 8 | 94 |

EXAMPLE 7

Preparation of micro-particles containing carbinoxamine maleate

Example 1 was repeated except that theophylline was replaced by 5 g of carbinoxamine maleate. The dissolution rate of the particles was determined and found to be as follows:

| Time (h) | % Release |
| --- | --- |
| 0.5 | 20 |
| 1 | 25 |
| 2 | 30 |
| 3 | 45 |
| 4 | 55 |
| 5 | 65 |
| 6 | 70 |
| 7 | 73 |
| 8 | 78 |

EXAMPLE 8

Preparation of micro-particles containing guaiphenesin

Example 1 was repeated except that theophylline was replaced by guaiphenesin (12.5 g). The polymer solution consisted of Ethocel TM 4 cps dissolved in ether to give a concentration of 25% w/v.

The external phase consisted of an aqueous solution of sorbitol 70% w/w (sorbitol solution B.P.)

Upon removal of the solvent of the internal phase the particles or "pharmasomes" remained suspended in the sorbitol solution. The particles were harvested by decanting the sorbitol solution. The dissolution rate of the particles was determined and was found to be as follows:

| Time (h) | % Release |
|---|---|
| 0.5 | 50 |
| 1 | 55 |
| 2 | 61 |
| 3 | 64 |
| 4 | 70 |
| 5 | 76 |
| 6 | 81 |
| 7 | 87 |
| 8 | 93 |

EXAMPLE 9

Example 8 was repeated without decanting the sorbitol solution. The suspension thereby obtained was flavored and made up to the required strength for use as an oral suspension.

EXAMPLE 10

Preparation of micro-particles containing erythromycin base

Example 1 was repeated except that theophylline was replaced by erythromycin base. The polymer used was a mixture of cellulose acetate butyrate and cellulose acetate phthalate in a ratio of 2:1. The dissolution rate of the particles was determined and was found to be as follows:

| Time (h) | % Release |
|---|---|
| 0.5 | 20 |
| 1 | 30 |
| 2 | 40 |
| 3 | 55 |
| 4 | 70 |
| 5 | 78 |
| 6 | 87 |
| 7 | 95 |

Other mixed polymers were used in the internal phase and proved successful in achieving a 100% release of the active ingredient from the particles formed. Examples of mixed polymers used were as follows:

| Polymer | Ratio |
|---|---|
| Cellulose acetate butyrate/polyvinylpyrrolidone | 9:1 |
| Cellulose acetate butyrate/polyvinylpyrrolidone | 4:1 |
| Cellulose acetate butyrate/poly (methyl methacylic acid) | 1:1 |
| Cellulose acetate butyrate/Poly (methyl methacylic acid) | 3:1 |
| Eudragit RS TM /Eudragit RL TM | 9:1 |
| Ethocel TM /polyvinylpyrrolidone | 9:1 |

EXAMPLE 11

Preparation of theophylline syrup

Particles prepared according to Example 1 were suspended in a sugar solution in water (66%) to obtain a theophylline syrup containing 200 mg of theophylline per 5 ml of syrup. When administered orally the normally bitter taste of theophylline was completely masked.

Pharmacological Data

Figure 3:
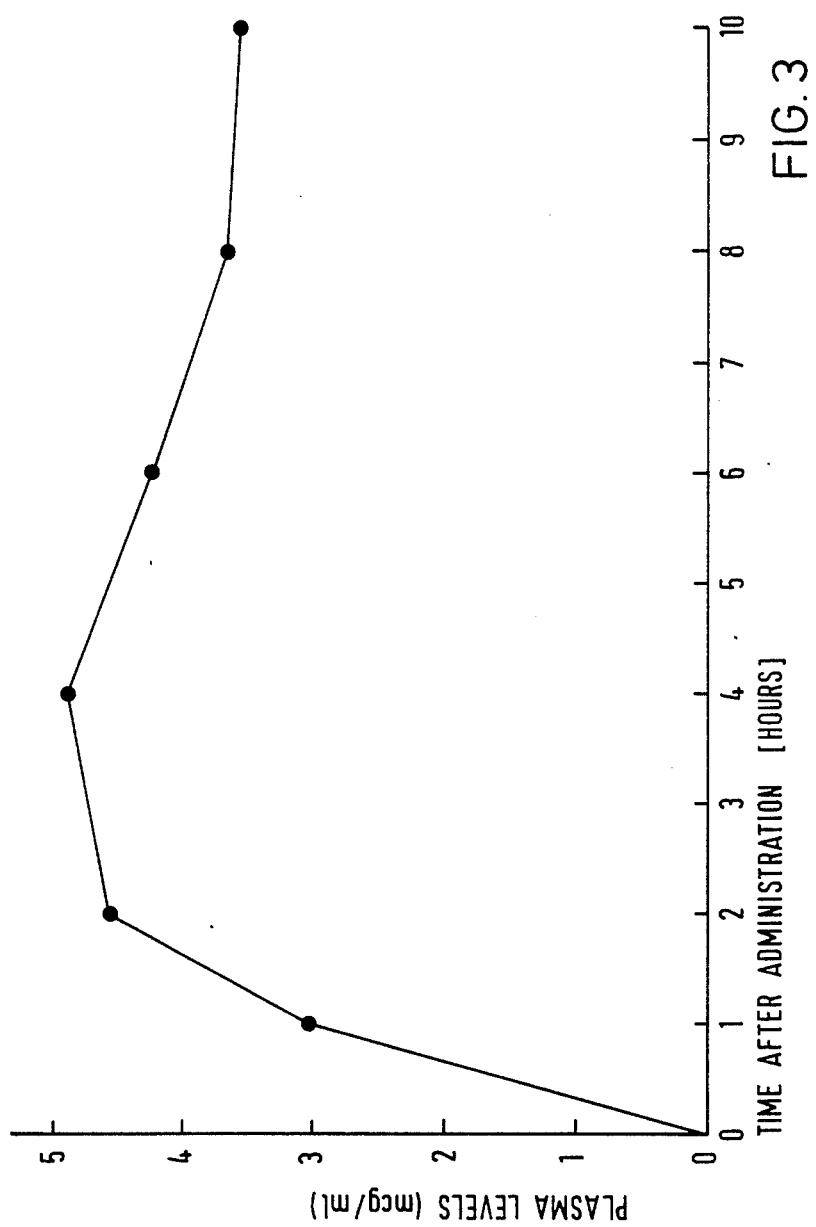
FIG. 3 is a graph of plasma levels (mcg/ml) versus time after administration for a syrup containing "pharmasomes" containing theophylline.

The plasma level profile of theophylline was obtained from the mean values obtained for two subjects according to the data listed in Tables 1 and 2 below. FIG. 3 is a graph of plasma levels (mcg/ml) versus time after administration (hours) for the theophylline syrup based on the values indicated in Tables 1 and 2.

It will be observed from the accompanying FIG. 3 and Tables 1 and 2 that the plasma levels after 10 hours are not significantly different from the plasma levels after one hour. Accordingly, the graph shows a prolonged absorption phase with a minimum of fluctuation of plasma levels over 10 hours. Normally, theophylline (rapid or immediate release) peaks at 2 hours. The apparent biological half-life of theophylline has been found to range from 4-9 hours. One would normally expect half the peak plasma levels by 7 hours and approximately one third of the peak plasma levels by 10 hours.

These results suggest that the syrup prepared according to Example 11 could potentially be dosed quite safely at intervals of 12 hours i.e. twice daily. This is half the dosage frequency of conventional non-sustained or immediate release theophylline.

TABLE 1

BLOOD LEVEL STUDY RESULTS - SUMMARY OF PHARMACOKINETIC DATA
THEOPHYLLINE - 600 mg S.D.
PLASMA LEVELS mcg/ml

| | HOURS AFTER ADMINISTRATION | | | | | | |
|---|---|---|---|---|---|---|---|
| SUBJ | 0.00 | 1.00 | 2.00 | 4.00 | 6.00 | 8.00 | 10.00 |
| 1 | 0.00 | 3.15 | 4.25 | 4.70 | 3.45 | 3.00 | 2.85 |
| 2 | 0.00 | 2.90 | 4.85 | 5.05 | 5.00 | 4.30 | 4.25 |
| MEAN | 0.00 | 3.03 | 4.55 | 4.88 | 4.23 | 3.65 | 3.55 |
| ST DEV | 0.00 | 0.18 | 0.42 | 0.25 | 1.10 | 0.92 | 0.99 |
| CV (%)* | 0.00 | 5.84 | 9.32 | 5.08 | 25.94 | 25.18 | 27.89 |
| MAX | 0.00 | 3.15 | 4.85 | 5.05 | 5.00 | 4.30 | 4.25 |
| MIN | 0.00 | 2.90 | 4.25 | 4.70 | 3.45 | 3.00 | 2.85 |

*Coefficient of variation

TABLE 2

THEOPHYLLINE - 600 mg S.D.
PHARMACOKINETIC PARAMETERS

| | AUC* (0.00–10.00 H) | PEAKING TIME T(max) | PEAK HEIGHT C(max) | C(max)/C(min) AT 10.00 HOURS | ELIMINATION RATE K EL | HALF-LIFE T½ |
|---|---|---|---|---|---|---|
| 1 | 34.67 | 4.00 | 4.70 | 1.65 | 0.05 | 14.51 |
| 2 | 43.13 | 4.00 | 5.05 | 1.19 | 0.03 | 20.74 |
| MEAN | 38.90 | 4.00 | 4.88 | 1.42 | 0.04 | 17.62 |
| ST DEV | 5.98 | 0.00 | 0.25 | 0.33 | 0.01 | 4.21 |
| CV (%) | 15.36 | 0.00 | 5.08 | 22.91 | 25.00 | 25.00 |
| BASED ON BLOOD LEVEL CURVE | | | | | | |
| MEAN | | 4.00 | 4.88 | 1.37 | | |

*Area under curve

EXAMPLE 12

Theophylline Suspension

Theophylline micro-particles "pharmasomes" (prepared as per Example 1) were suspended in a liquid vehicle consisting of:

| | |
|---|---|
| 70% Sorbitol Solution | 89.9% by weight |
| Glycerin | 10.0% by weight |
| Polysorbate-80 TM | 0.1% by weight | to give a suspension containing 200 mg theophylline per 5 ml.

Samples of the suspension were stored at room temperature and tested at intervals to determine the stability of the "pharmasomes" in suspension.

At the time of preparation the assayed content of theophylline was 188.4 mg/5 ml and after 15 weeks it was 190.5 mg/5 ml indicating that there had been no chemical breakdown of the drug.

Figure 4:
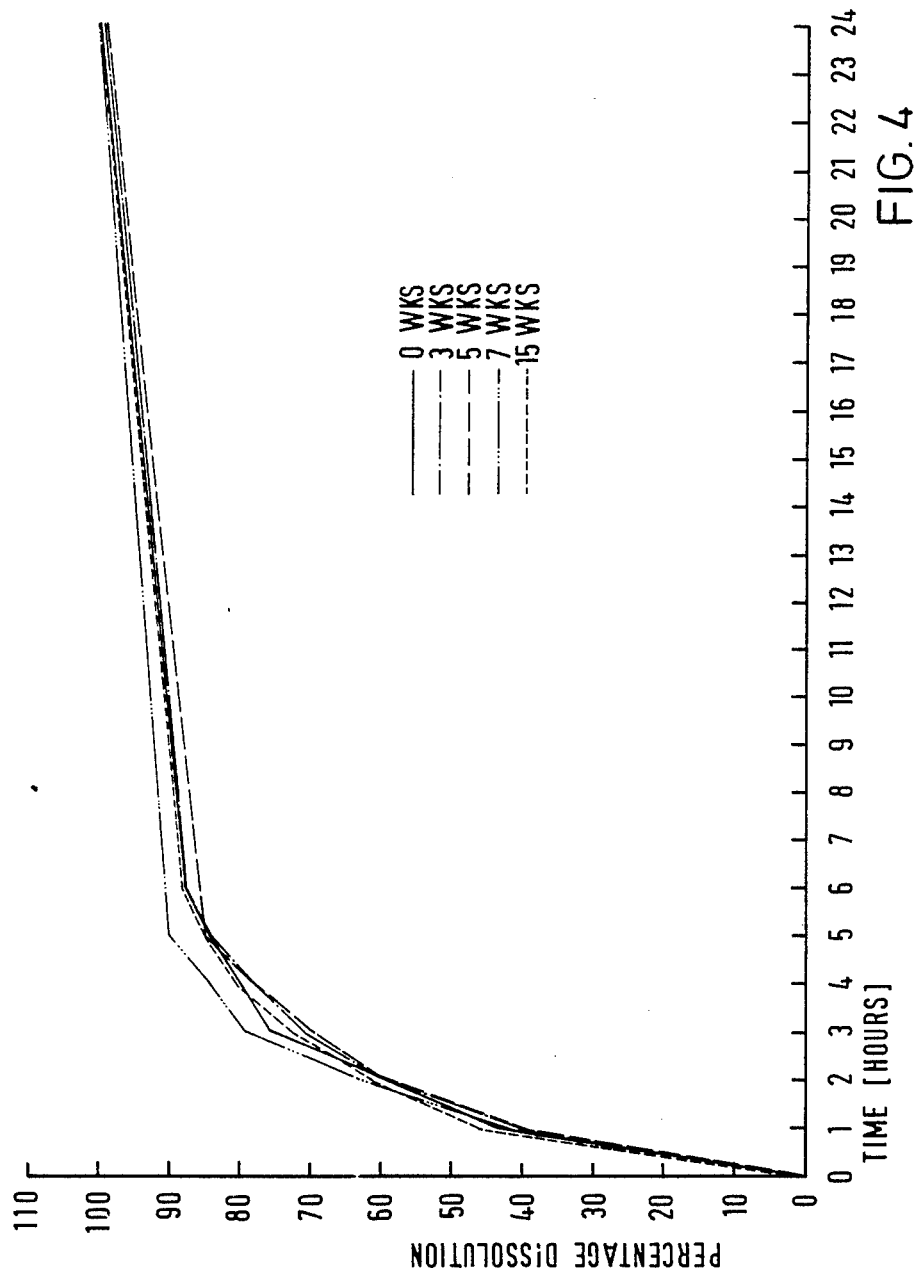
FIG. 4 is a graph of percentage dissolution versus time for a suspension containing "pharmasomes" containing theophylline.

The dissolution rate was also tested over a 15 week period and the results are summarized in Table 3 and FIG. 4.

In summary the data shows that the suspension retains its potency and dissolution characteristics for at least 15 weeks after preparation.

Pharmacological Data

Figure 5:
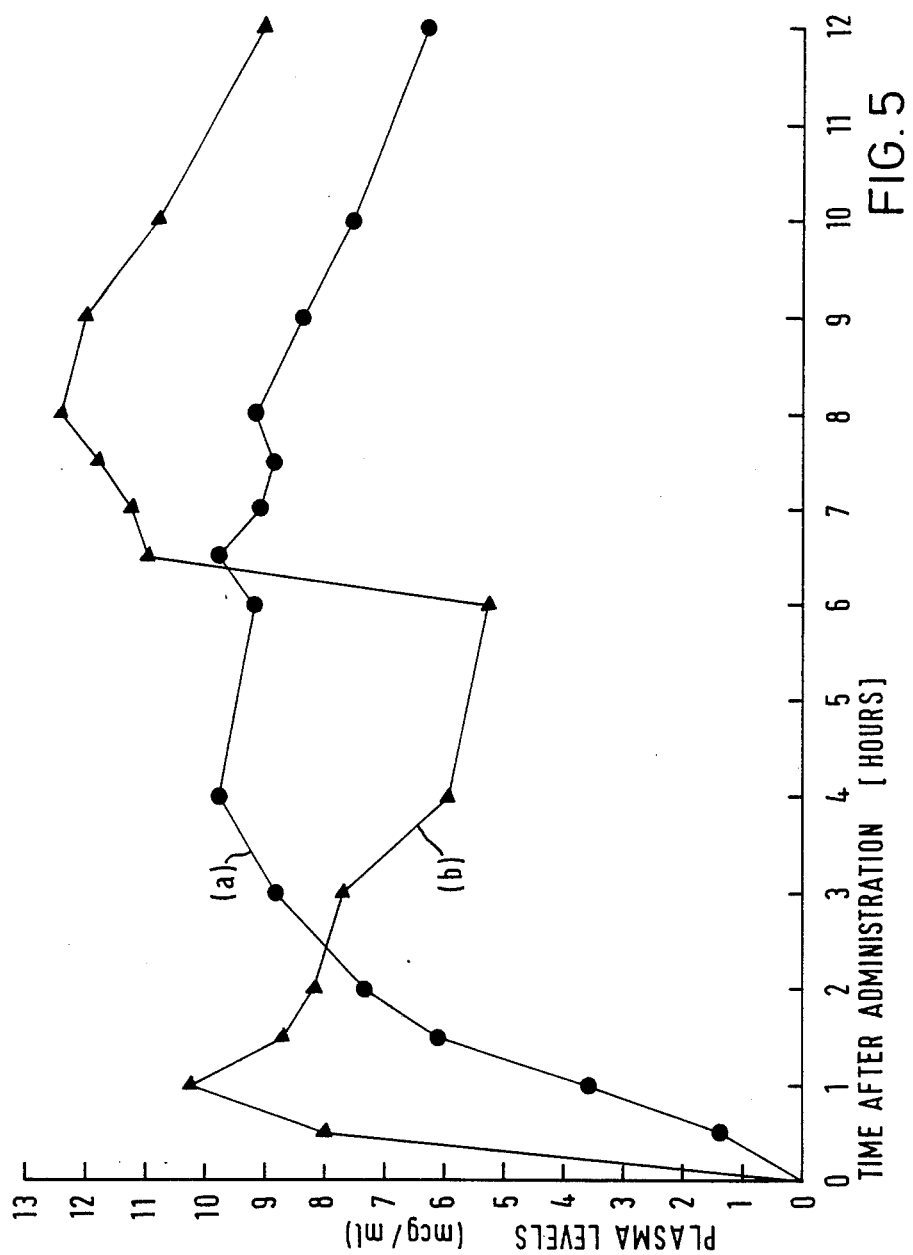
FIG. 5 is a comparison graph of plasma levels (mcg/ml) versus time after administration for a suspension containing "pharmasomes" containing theophylline and a conventional theophylline syrup.

The suspension prepared as per Example 12 was tested in a six subject bioavailability study at a dose of 720 mg (18 ml) versus a conventional syrup (Somophylline a product of Fisons) given as two doses of 360 mg at 0 and 6 hours. The results are summarized in Table 4 and FIG. 5. In FIG. 5 curve (a) represents the suspension of Example 12 and curve (b) represents the Somophylline syrup used as reference.

TABLE 3

THEOPYLLINE SUSPENSION OF EXAMPLE 12 (200 mg/5 ml)
STABILITY OF DISSOLUTION
Pecentage Dissolution

| | TIME (HOURS) | | | | | | | |
|---|---|---|---|---|---|---|---|---|
| | 0.00 | 1.00 | 2.00 | 3.00 | 4.00 | 5.00 | 6.00 | 24.00 |
| 0 wks | 0.00 | 43.30 | 59.20 | 75.60 | 80.00 | 84.30 | 87.70 | 100.00 |
| 3 wks | 0.00 | 39.50 | 59.10 | 70.70 | 77.90 | 84.20 | 87.70 | 99.50 |
| 5 wks | 0.00 | 40.00 | 60.10 | 69.80 | 78.20 | 85.10 | 85.90 | 99.00 |
| 7 wks | 0.00 | 42.00 | 63.00 | 79.20 | 84.20 | 90.00 | 90.60 | 100.00 |
| 15 wks | 0.00 | 45.80 | 60.90 | 72.50 | 80.70 | 84.90 | 88.00 | 99.90 |

TABLE 4

MEAN THEOPHYLLINE PLASMA CONCENTRATION (mcg/ml)

| TIME (h) | SOMOPHYLLINE | THEOPHYLLINE SUSPENSION |
|---|---|---|
| 0.0 | 0.0 | 0.0 |
| 0.5 | 7.98 | 1.38 |
| 1.0 | 10.24 | 3.57 |
| 1.5 | 8.68 | 6.09 |
| 2.0 | 8.17 | 7.31 |
| 3.0 | 7.68 | 8.81 |
| 4.0 | 5.93 | 9.75 |
| 6.0 | 5.25 | 9.17 |
| 6.5 | 10.94 | 9.75 |
| 7.0 | 11.20 | 9.08 |
| 7.5 | 11.75 | 8.84 |
| 8.0 | 12.37 | 9.14 |
| 9.0 | 11.98 | 8.37 |
| 10.0 | 10.76 | 7.52 |
| 12.0 | 8.99 | 6.26 |

The data clearly shows that although the theophylline suspension of Example 12 is slightly less bioavailable (87%) than the reference, the time to peak and the duration of significant blood levels is indicative of a twice daily dosage regimen. The usual dosage regimen for theophylline of four times per day.

EXAMPLES 13 and 14

Theophylline micro-particle "pharmasomes" were prepared according to Example 1 and screened into two fractions:

Example 13—micro-particles having an average particle size of less than 90 microns Example 14—micro-particles having an average particle size of greater than 90 microns.

The "pharmasomes" were suspended in a vehicle made up of:

| The "pharmasomes" were suspended in a vehicle made up of: | |
|---|---|
| | % by weight |
| 70% Sorbitol Solution | 85.3 |
| Avicel RC 591 TM | 0.7 |
| Potassium Sorbate | 0.3 |
| Titanium Dioxide 25% (in 70% Sorbitol) | 2.7 |
| Simethicone TM 10% Emulsion | 0.01 |
| Glycerin | 10.8 |
| Citric Acid | 0.3 |
| Sodium Lauryl Sulphate | 0.04 | to produce a suspension containing 300 mg theophylline per 5 ml.

Pharmacological Data

Figure 6:
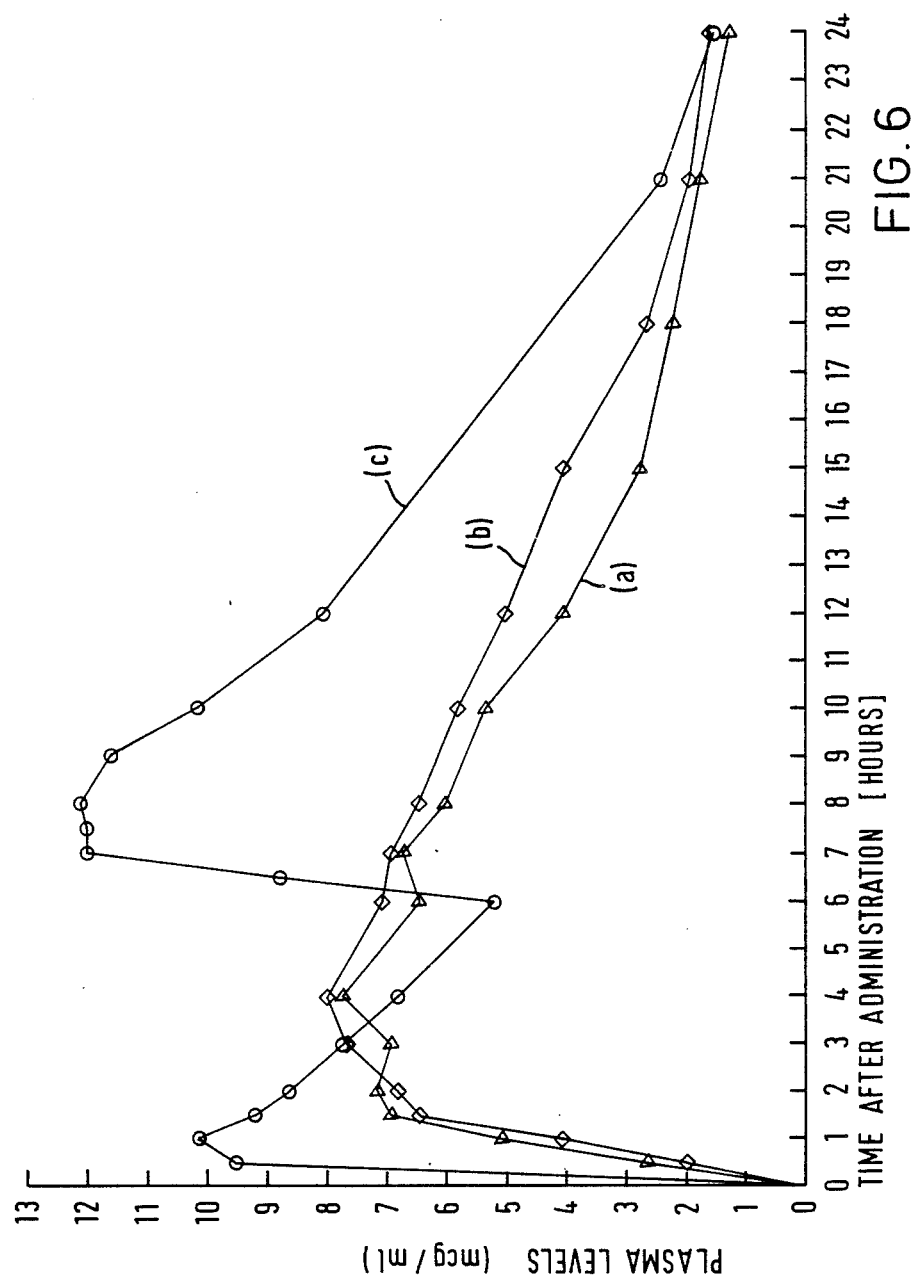
FIG. 6 is a comparison graph of plasma levels (mcg/ml) versus time after administration for two suspensions containing different sized theophylline containing "pharmasomes" and a conventional theophylline syrup.

The suspensions of Examples 13 and 14 were tested for bioavailability in four subjects at a dose of 690 mg (11.5 ml) for the syrups of Examples 13 and 14 versus a conventional syrup (Somophylline a product of Fisons) given as two doses of 320 mg at 0 and 6 hours. The results are summarized in Table 5 and FIG. 6. In FIG. 6, curve (a) represents the suspension of Example 13, curve (b) the suspension of Example 14 and curve (c) the Somophylline syrup used as reference.

TABLE 5

MEAN THEOPHYLLIN PLASMA CONCENTRATIONS - mcg/ml

| Time (h) | Somophylline | Suspension of Example 13 | Suspension of Example 14 |
| --- | --- | --- | --- |
| 0 | 0 | 0 | 0 |
| 0.5 | 9.53 | 2.65 | 1.98 |
| 1 | 10.14 | 5.08 | 4.07 |
| 1.5 | 9.21 | 6.94 | 6.45 |
| 2 | 8.64 | 7.16 | 6.81 |
| 3 | 7.74 | 6.93 | 7.67 |
| 4 | 6.82 | 7.74 | 7.99 |
| 6 | 5.21 | 6.46 | 7.08 |
| 6.5 | 8.79 | — | — |
| 7 | 12.00 | 6.74 | 6.93 |
| 7.5 | 12.01 | — | — |
| 8 | 12.11 | 6.03 | 6.47 |
| 9 | 11.61 | — | — |
| 10 | 10.17 | 5.35 | 5.82 |
| 12 | 8.07 | 4.06 | 5.02 |
| 15 | — | 2.77 | 4.04 |
| 18 | — | 2.22 | 2.67 |
| 21 | 2.44 | 1.79 | 1.95 |
| 24 | 1.55 | 1.28 | 1.59 |

Figure 7:
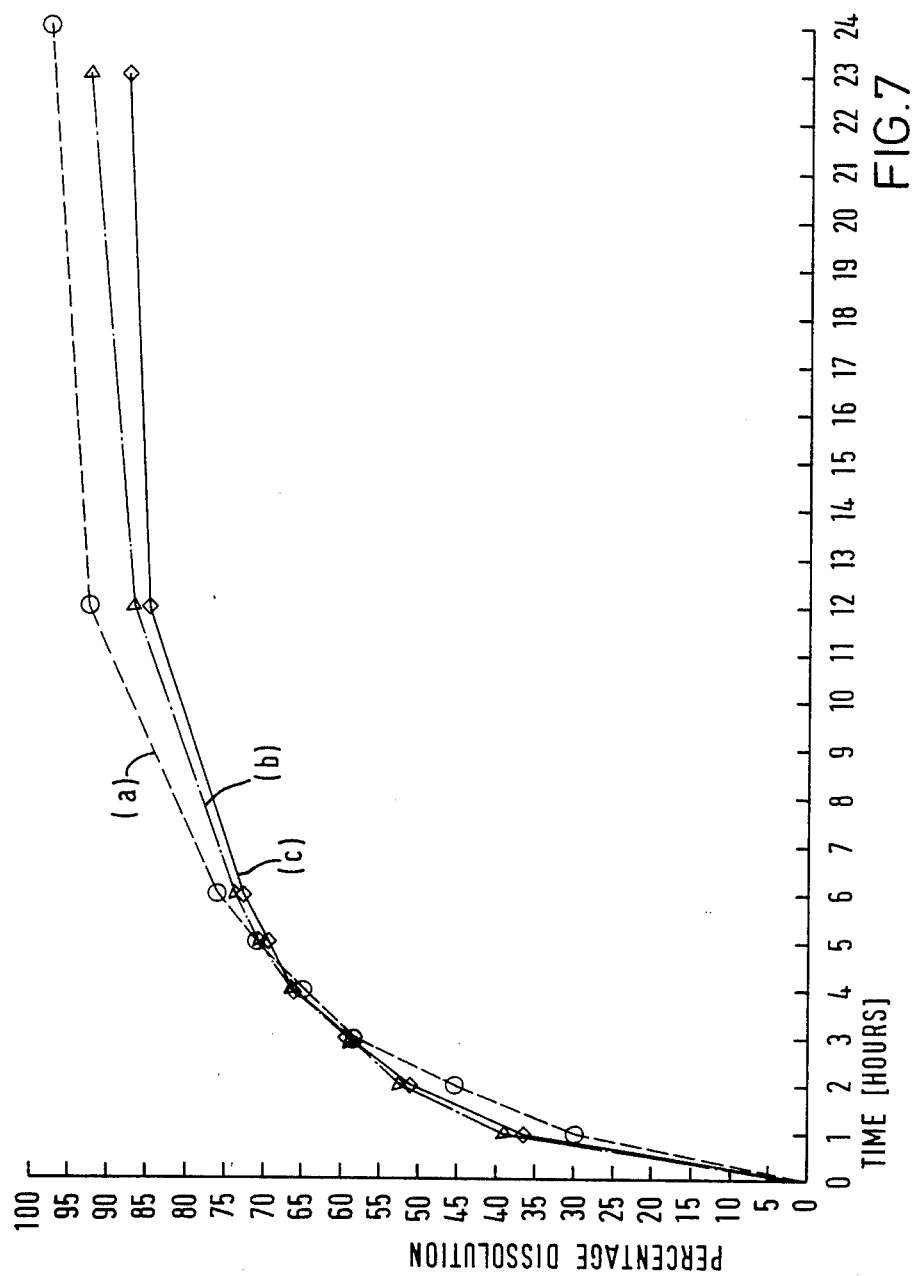
FIG. 7 is a graph of percentage dissolution versus time for three different suspensions containing theophylline containing "pharmasomes"

The results confirm the findings for Example 12 as indicated in FIG. 7, wherein curve (a) represents the suspension of Example 12, curve (b) the suspension of Example 13 and curve (c) the suspension of Example 14.

EXAMPLE 15

ACETAMINOPHEN SUSPENSION

Acetaminophen "pharmasomes" prepared as per Example 2 were suspended in a liquid vehicle prepared as per Example 12 to give a suspension containing 300 mg of acetaminophen per 5 ml.

The suspension was stored at room temperature and tested at certain intervals for 30 weeks.

At the time of preparation the assayed content was 299.8 mg (acetaminophen) per 5 ml and after 30 weeks was 297.9 mg/5 ml indicating that there was no significant loss of activity.

During the above time period the dissolution was also tested and the results are given in Table 6.

TABLE 6

PERCENTAGE DISOLUTION

| | TIME (h) | | | | | | |
| --- | --- | --- | --- | --- | --- | --- | --- |
| | 0.00 | 1.00 | 2.00 | 3.00 | 4.00 | 5.00 | 6.00 |
| 0 wks | 0.00 | 56.50 | 70.60 | 76.00 | 81.30 | 83.80 | 86.30 |
| 2 wks | 0.00 | 58.40 | 71.80 | 80.40 | 81.70 | 86.40 | 87.90 |
| 5 wks | 0.00 | 56.90 | 72.50 | 77.20 | 80.40 | 83.90 | 84.40 |
| 7 wks | 0.00 | 55.30 | 69.10 | 75.40 | 80.30 | 82.90 | 84.70 |
| 15 wks | 0.00 | 58.90 | 69.30 | 76.78 | 80.60 | 82.80 | 84.30 |
| 30 wks | 0.00 | 58.10 | 71.50 | 76.90 | 81.90 | 84.70 | 87.30 |

Figure 8:
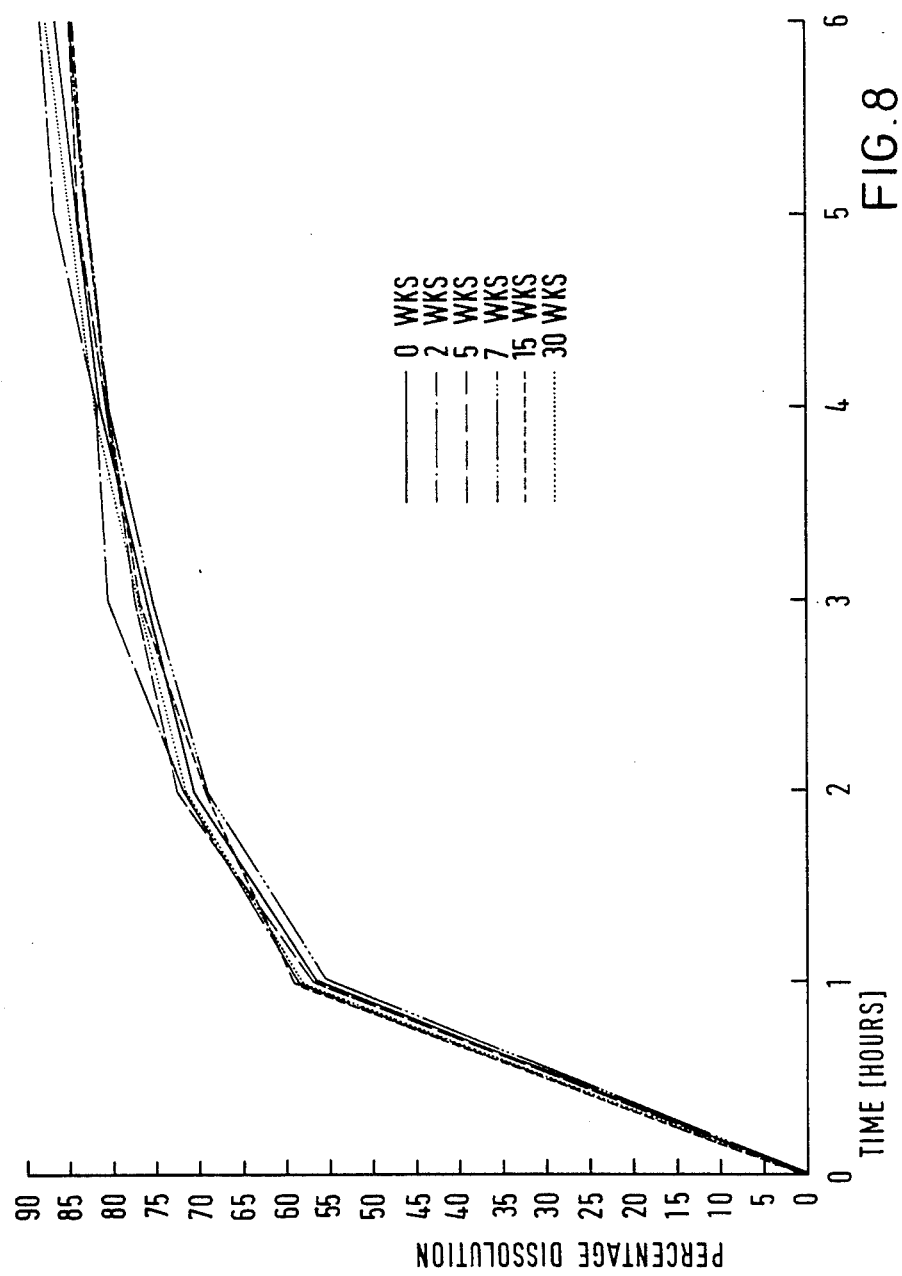
FIG. 8 is a graph of percentage dissolution versus time for a suspension containing acetaminophen containing "pharmasomes"

A graphic representation of these results is shown in FIG. 8.

The suspension was tested for bioavailability in 6 subjects at a dose of 1000 mg versus a reference solution (Dozol-Elixir TM a product of Rice Steele) which was given as two divided doses of 500 mg. The results are given in Table 7.

TABLE 7

MEAN ACETAMINOPHEN PLASMA CONCENTRATIONS (mcg/ml)

| Time (h) | Reference (DOZOL) | Suspension of Example 15 |
| --- | --- | --- |
| 0.0 | 0.0 | 0.0 |
| 0.5 | 7.74 | 3.44 |
| 1.0 | 6.49 | 6.05 |
| 2.0 | 4.14 | 7.36 |
| 3.0 | 3.04 | 5.80 |
| 4.0 | 2.04 | 4.60 |
| 6.0 | 1.08 | 3.15 |
| 6.5 | 5.33 | 2.65 |
| 7.0 | 5.88 | 2.26 |
| 8.0 | 4.79 | 1.88 |
| 9.0 | 4.00 | 1.63 |
| 10.0 | 3.05 | 1.44 |
| 12.0 | 1.81 | 1.06 |
| 14.0 | 1.10 | 0.72 |
| 16.0 | 0.69 | 0.49 |
| 24.0 | 0.18 | 0.14 |

Figure 9:
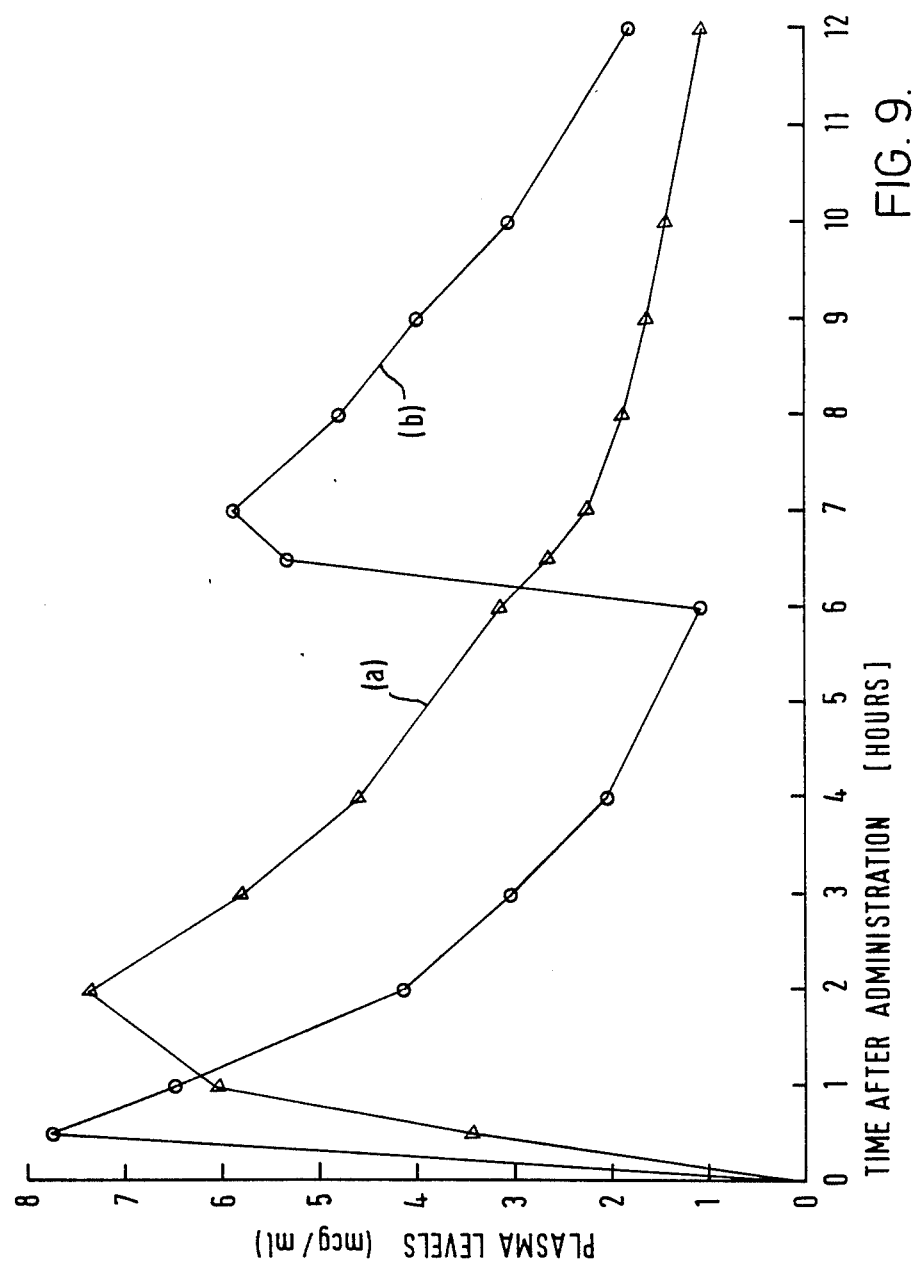
FIG. 9 is a comparison graph of plasma levels (mcg/ml) versus time after administration for a suspension containing acetaminophen containing "pharmasomes" and a conventional acetaminophen syrup.

A graphic representation is given in FIG. 9, wherein curve (b) represents the conventional Elixir and curve (a) represents the suspension of Example 15.

The data shows that although the suspension of Example 15 is slightly less bioavailable (90%) than the reference, the blood level is maintained for almost twice as long equating to halving of the dosage frequency.

EXAMPLE 16

"Pharmasomes" were prepared as per Example 2 and suspended in liquid as per Example 13 to give a suspension containing 320 mg per 5 ml. This suspension was tested for bioavailability in 6 subjects versus a conventional acetaminophen preparation (Tylenol TM Elixir a product of Johnson and Johnson) as reference. A single dose of acetaminophen "pharmasomes" 2000 mg (31.25 ml) was administered and two doses of Tylenol (1000 mg) were administered at 0 and 6 hours. The results are given in Table 8.

TABLE 8

MEAN ACETAMINOPHEN PLASMA CONCENTRATIONS (mcg/ml)

| TIME (h) | Reference (Tylenol Elixir) | Suspension of Example 16 |
| --- | --- | --- |
| 0.0 | 0.0 | 0.0 |
| 0.5 | 14.33 | 8.27 |
| 1.0 | 14.05 | 15.09 |
| 2.0 | 6.69 | 14.43 |
| 3.0 | 6.95 | 13.24 |
| 4.0 | 4.93 | 11.53 |
| 4.5 | 15.53 | 9.52 |
| 5.0 | 14.67 | 8.08 |
| 6.0 | 12.72 | 6.10 |
| 7.0 | 8.92 | 4.43 |
| 8.0 | 6.61 | 3.54 |
| 10.0 | 3.64 | 2.43 |
| 12.0 | 2.17 | 1.10 |
| 14.0 | 1.31 | 1.10 |
| 16.0 | 0.77 | 0.68 |
| 24.0 | 0.02 | 0.17 |

Figure 10:
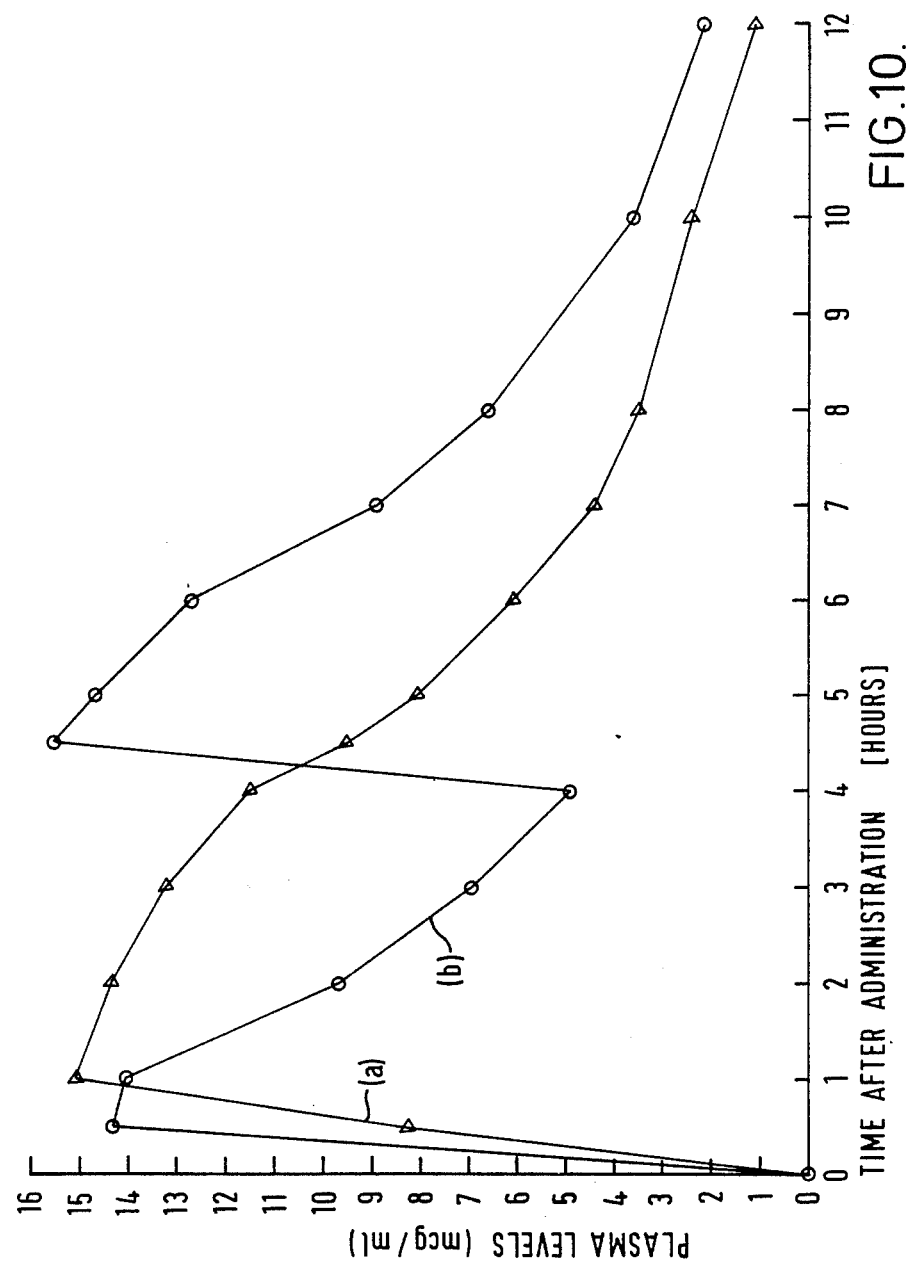
FIG. 10 is a comparison graph of plasma levels (mcg/ml) versus time after administration for a suspension containing acetaminophen containing "pharmasomes" and a conventional acetaminophen syrup.

The results are presented graphically in FIG. 10 wherein curve (a) corresponds to the suspension of Example 16 and curve (b) corresponds to the reference Elixir. The prolonged absorption profile again can be seen with no significant loss in bioavailability, indicating a reduced dosage frequency.

EXAMPLE 17

"Pharmasomes" were prepared as per Example 2 with cellulose acetate being substituted for the cellulose acetate butyrate. The suspension was prepared as per Example 16. The suspension was tested in a 6 subject bioavailability study at a single dose of 2000 mg against a reference solution (Tylenol Elixir) given as two 1000 mg doses. The results are given in Table 9.

TABLE 9

MEAN ACETAMINOPHEN PLASMA CONCENTRATIONS (mcg/ml)

| TIME (h) | Tylenol Elixir 1 g × 2 | Suspension of Example 17 2 g × 1 |
|---|---|---|
| 0.0 | 0.00 | 0.00 |
| 0.5 | 12.30 | 5.11 |
| 0.75 | 12.88 | 7.07 |
| 1.0 | 12.29 | 9.15 |
| 1.5 | 10.17 | 12.01 |
| 2.0 | 8.19 | 12.47 |
| 3.0 | 6.00 | 11.17 |
| 4.0 | 4.5 | 9.40 |
| 4.5 | 13.54 | 8.37 |
| 4.75 | 14.00 | 8.04 |
| 5.0 | 13.02 | 7.55 |
| 5.5 | 13.09 | 6.57 |
| 6.0 | 11.20 | 5.71 |
| 7.0 | 8.17 | 4.54 |
| 8.0 | 5.98 | 3.76 |
| 10.0 | 3.42 | 2.66 |
| 12.0 | 1.98 | 1.60 |
| 14.0 | 1.24 | 1.03 |
| 16.0 | 0.82 | 0.83 |
| 24.0 | 0.26 | 0.39 |

Figure 11:
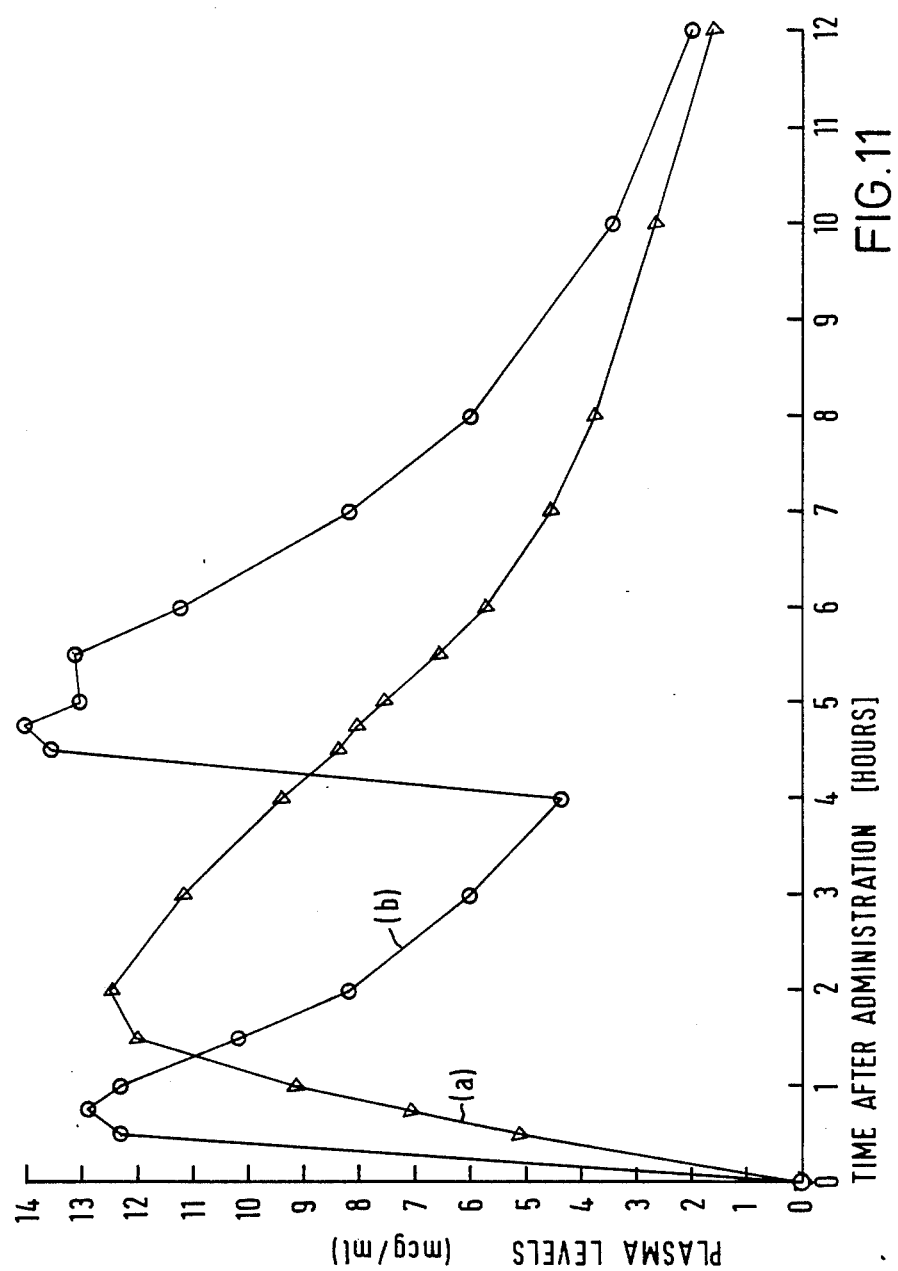
FIG. 11 is a comparison graph of plasma levels (mcg/ml) versus time after administration for a suspension containing acetaminophen containing "pharmasomes" and a conventional acetaminophen syrup.
Figure 12:
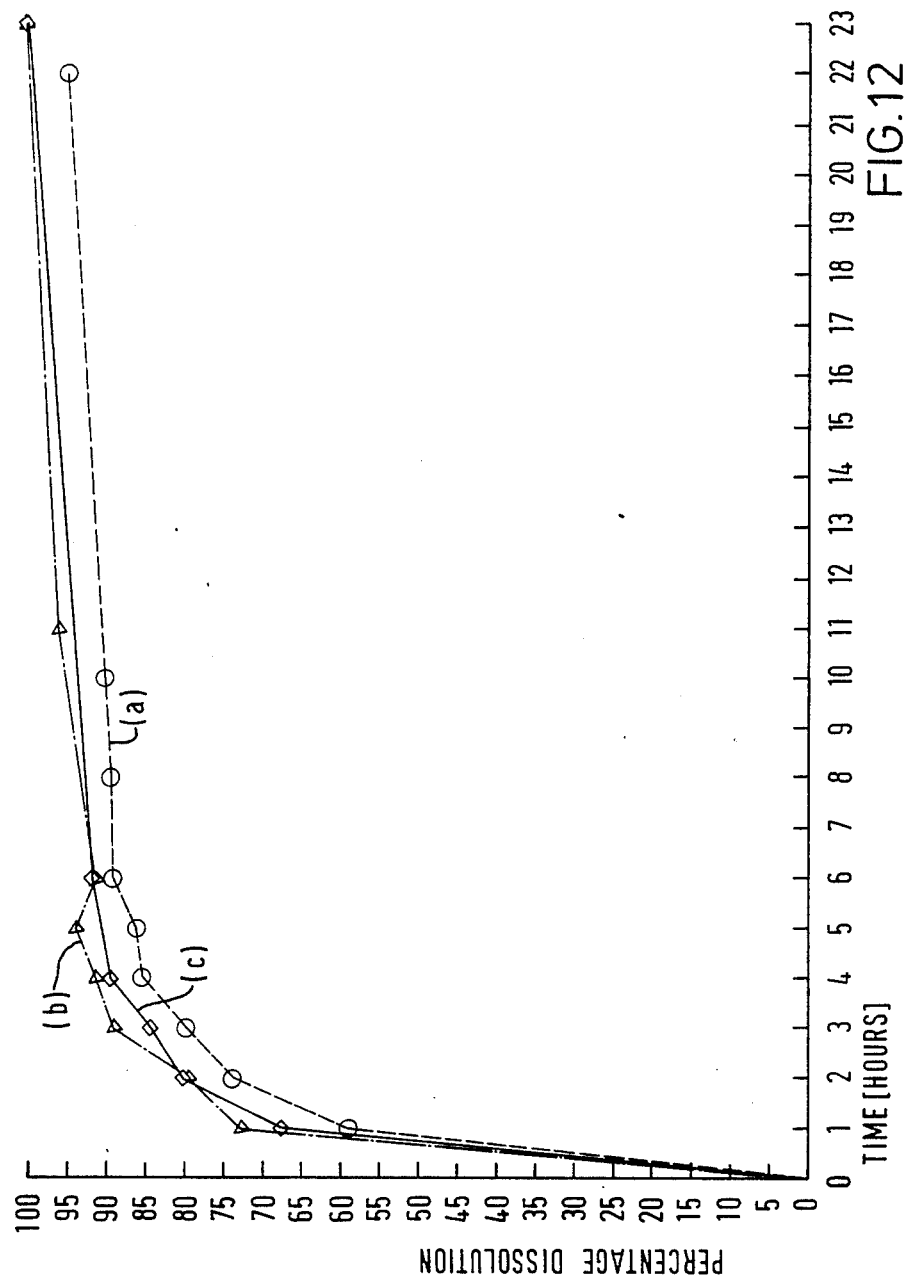
FIG. 12 is a graph of percentage dissolution versus time for three different suspensions containing acetaminophen containing "pharmasomes"

The figures given in Table 9 and accompanying FIGS. 11 and 12 again demonstrate the prolonged absorption nature of the product. In FIG. 11 curve (a) corresponds to the suspension of Example 19 and curve (b) corresponds to the reference Tylenol Elixir. In FIG. 12 curve (a) corresponds to the suspension of Example 15, curve (b) to the suspension of Example 16 and curve (c) to the suspension of Example 17.

EXAMPLE 18

Chewing gum containing micro-particles of Aspartame were prepared in the following manner.

An internal phase was prepared by dissolving ethylcellulose (45 cps) in sufficient ethanol to produce 200 g of solution. 100 g of Aspartame (particle size less than 60 microns) was dispersed in 300 g of acetone. The two liquids were then mixed by mechanical agitation. The external phase was prepared according to Example 1, 2 liters being required. The internal and external phase were mixed by mechanical agitation and then passed through an emulsifier. The emulsion was placed in a vacuum and the solvents (acetone and ethanol) evaporated. The aspartame/ethylcellulose micro-particles were harvested by centrifugation.

Figure 13:
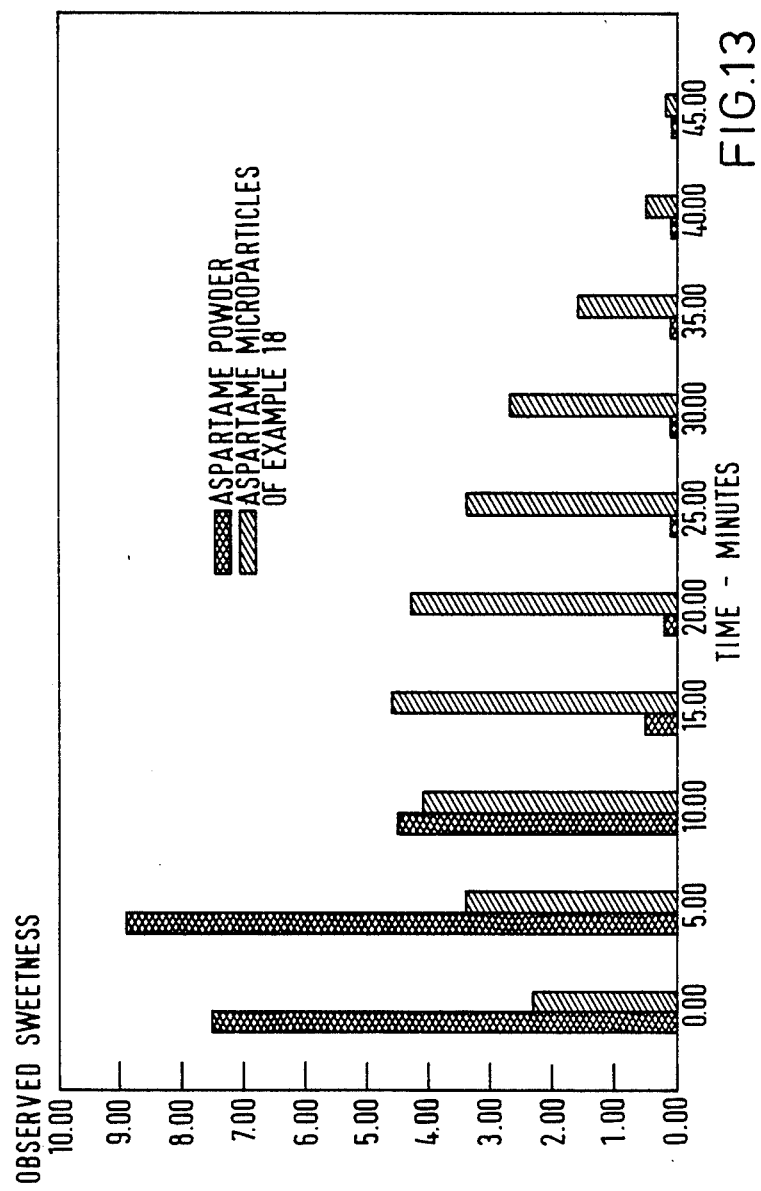
FIG. 13 is a comparison graph of observed sweetness versus time for chewing gum containing aspartame containing "pharmasomes" and chewing gum containing aspartame powder.

To evaluate the aspartame-containing "pharmasomes", unsweetened chewing gum was used. Pure aspartame powder and the prepared "pharmasomes" were folded into the gum to give a 0.2% concentration of aspartame. Both types of gum were chewed by a panel of 24 volunteers in a blind, crossover manner. The volunteers were asked to report their perception of the intensity (on a scale of 0 to 10) and duration of sweetness. On average the duration of sweetness for the pure aspartame-containing gum was 10 minutes. The gum containing the "pharmasomes" was perceived as being less intensely sweet but observably sweet for 30 minutes on average. The results are indicated in FIG. 13 which is a graphic representation of the aspartame sweetness test giving mean values for the testing panel of 24 volunteers.

EXAMPLE 19

Chewable Tablet Containing Acetaminophen

The following materials were mixed together:

| | |
|---|---|
| 1000 g | Acetaminophen "pharmasomes" - as per Example 2 (equivalent to 500 g of acetaminophen) |
| 250 g | Dipac TM (Sucrose 97%, Dextrins 3%) |
| 250 g | Mannitol |
| 5 g | Colloidal Silicon Dioxide |
| 25 g | Maize Starch |
| 20 g | Magnesium Stearate |
| 15 g | Orange Flavor |
| 35 g | Orange Color |

The blend was compressed at a weight of 960 mg into tablets each containing 300 mg of acetaminophen. The tablets were pleasant to chew and the dissolution characteristics of the "pharmasomes" were unchanged as shown in Table 10 and FIG. 14.

TABLE 10

| | DISSOLUTION RATE | |
|---|---|---|
| TIME (h) | "PHARMASOMES" | TABLETS |
| 1 | 58.7% | 59.2% |
| 3 | 79.8% | 80.7% |
| 6 | 95.6% | 95.8% |

Figure 14:
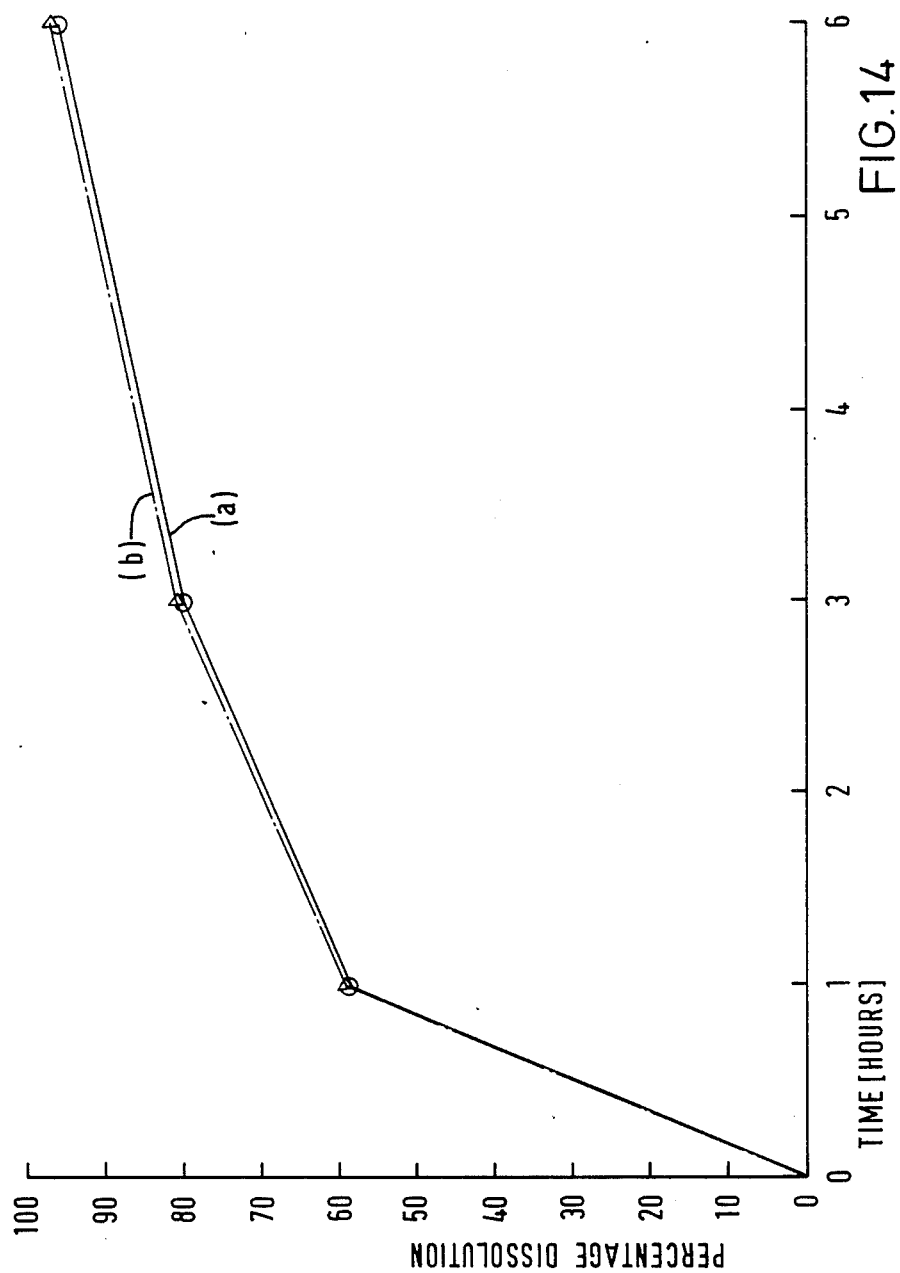
FIG. 14 is a graph of percentage dissolution versus time for "pharmasomes" containing acetaminophen and for chewable tablets prepared therefrom.

In FIG. 14 curve (a) corresponds to the dissolution pattern of the "pharmasomes" of Example 19 and curve (b) to the chewable tablets prepared therefrom.

EXAMPLE 20

"Melt" Tablets Containing Acetaminophen

Melt tablets are similar to chewable tablets except that they disintegrate rapidly in the mouth and do not need to be chewed. Such tablets were prepared as follows:

| | |
|---|---|
| 1000 g | Acetaminophen "pharmasomes" (as per Example 2) (equivalent to 500 g acetaminophen) |
| 50 g | Mannitol |
| 250 g | Microcrystalline Cellulose |
| 30 g | Strawberry Flavor |
| 15 g | Red Color |
| 60 g | Cross-Povidone TM |
| 5 g | Sodium Lauryl Sulphate |
| 30 g | Caboxymethyl Starch |
| 15 g | Magnesium Stearate |
| 15 g | Talc |

The blend was compressed at a weight of 882 mg to give tablets each containing 300 mg of acetaminophen. The disintegration time of the tablets was less than 30 seconds and the dissolution rate of the "pharmasomes" was unchanged as indicated in Table 11 and FIG. 15.

TABLE 11

| | DISSOLUTION RATE | |
|---|---|---|
| TIME (h) | "PHARMASOMES" | TABLETS |
| 1 | 58.7% | 60.1% |
| 3 | 79.8% | 81.2% |

TABLE 11-continued

| TIME (h) | DISSOLUTION RATE "PHARMASOMES" | TABLETS |
|---|---|---|
| 6 | 95.6% | 95.5% |

Figure 15:
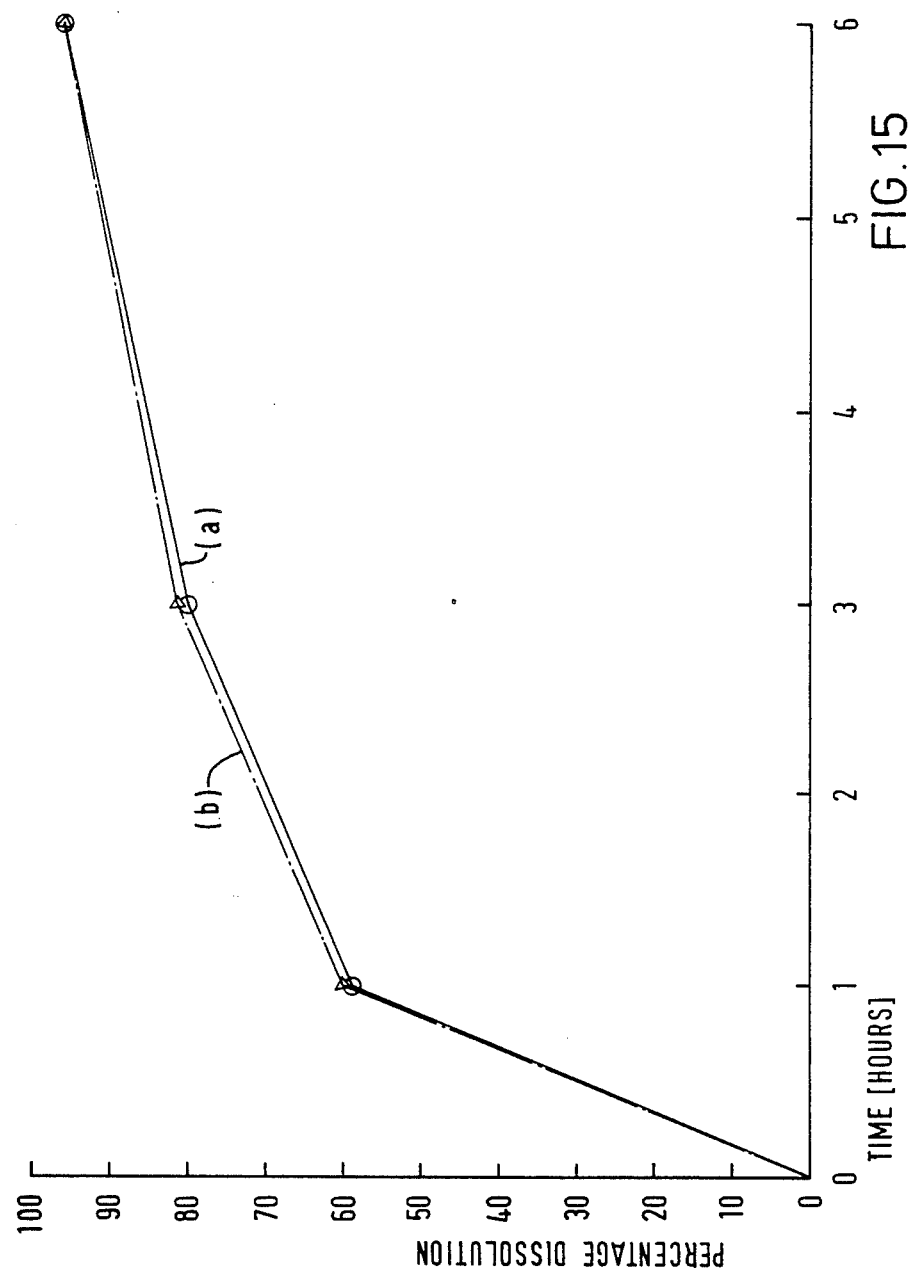
FIG. 15 is a graph of percentage dissolution versus time for "pharmasomes" containing acetaminophen and for melt tablets prepared therefrom.

In FIG. 15 curve (a) corresponds to the dissolution pattern for the "pharmasomes" of Example 20 and curve (b) to the melt tablets prepared therefrom.

EXAMPLE 21

Capsules Containing Nifedipine

Figure 16:
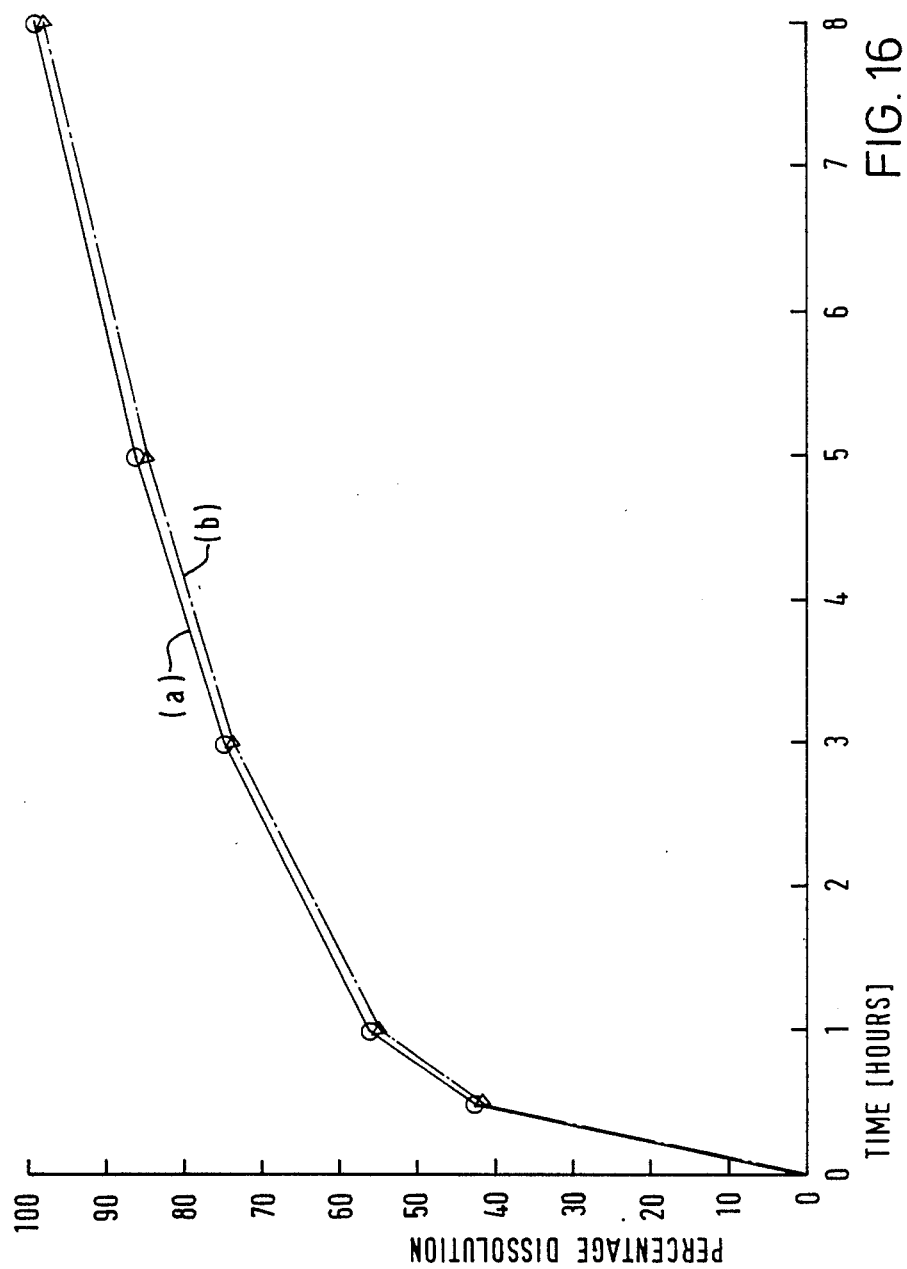
FIG. 16 is a graph of percentage dissolution versus time for "pharmasomes" containing nifedipine and for capsules prepared therefrom.

"Pharmasomes" were prepared as per Example 3. By nature they were free flowing and only 0.5% magnesium stearate needed to be added to prevent sticking during capsule filling. The equivalent of 20 mg of nifedipine was encapsulated into size No. 4, two piece hard gelatin capsules. The dissolution rate remained unchanged as shown in Table 12 and FIG. 16. In FIG. 16 curve (a) corresponds to the dissolution pattern for the "pharmasomes" of Example 21 and curve (b) to the capsules prepared therefrom.

TABLE 12

| TIME (h) | DISSOLUTION RATE "PHARMASOMES" | CAPSULES |
|---|---|---|
| 0.5 | 42.6% | 41.7% |
| 1 | 56.1% | 54.9% |
| 3 | 74.6% | 73.6% |
| 5 | 85.9% | 84.4% |
| 8 | 98.7% | 97.6% |

EXAMPLE 22

Non-Aqueous Suspension of Potassium Chloride

A non-aqueous suspension of potassium chloride-containing "pharmasomes" was prepared, having a concentration of potassium chloride of 300 mg/5 ml and which in addition to the "pharmasomes" contained the following ingredients:

| | |
|---|---|
| Oil USP (Soy, cotton seed) | 425.00 ml |
| Sorbitol Powder USP | 100.00 g |
| Aerosil R 972 TM | 12.50 g |
| Tenox GT 1 TM | 0.20 g |
| Citric Acid | 0.025 g |
| Chocolate flavor #396676 | 0.52 ml |
| Chocolate mint flavor #395496 | 0.37 ml |
| Flavor enhancer | 1.00 g |
| Brown Lake dye | 0.05 g |
| Titanium dioxide | 0.10 g |

The total volume of the suspension without the "pharmasomes" was 500 ml.

The Sorbitol powder USP and Aerosil R 972 TM (a product of Duphar, at Dutch company) were dry blended and then ball milled with the oil mix to produce an even dispersion. The Tenox GT 1 TM (a product of Tennessee Eastman Corp.) which is an anti-oxidant and the citric acid were dry blended and then dispersed with constant agitation into the oil mixture. The chocolate and chocolate mint flavors and the flavor enhancer were then dispersed into the oil mixture. Finally, the Brown Lake dye and the titanium dioxide were added to the oil mixture and the resultant mixture was agitated for one hour to ensure even dispersion of the various ingredients. An amount of potassium chloride-containing "pharmasomes", prepared according to the procedure described in Example 1 but substituting potassium chloride for theophylline, and equivalent to 300 mg potassium chloride per 5 ml was blended together with the oil mixture resulting in an evenly mixed suspension.

Although not wishing to be bound by any theoretical explanation of the invention, it is believed that the polymer substantially but not entirely coats the active ingredient, because a 100% release of active ingredient can be achieved even when an insoluble polymer is used.

While preferred embodiments of the invention have been shown and described, it will be understood by persons skilled in the art that various changes and modifications may be made thereto without departing from the spirit and scope thereof as defined by the following claims.

What is claimed is:

1. A controlled release taste-masked powder containing discrete micro-particles for use in edible, pharmaceutical and other controlled release compositions, said powder comprising particles containing theophylline as an active ingredient in intimate admixture with two polymers, cellulose acetate butyrate and polyvinylpyrrolidone, in an amount effective to provide a predetermined and controlled release of said active ingredient, each of said particles being in the form of a micromatrix with the active ingredient uniformly distributed throughout the matrix, but not entirely coated by the polymers, said particles having an average size of from 0.1 to 125 μm, being unlikely to be significantly degraded or ground by any chewing action, and wherein said predetermined release of active ingredient is suitable for twice daily administration.

2. A controlled release taste-masked powder containing discrete micro-particles for use in edible, pharmaceutical and other controlled release compositions, said powder comprising particles containing theophylline as an active ingredient in intimate admixture with at least two polymers, at least one of which is soluble and at least one of which is water insoluble, in an amount effective to provide a predetermined and controlled release of said active ingredient, each of said particles being in the form of a micromatrix with the active ingredient uniformly distributed throughout the matrix, but not entirely coated by the polymers, said particles having an average size of from 0.1 to 125 μm, being unlikely to be significantly degraded or ground by any chewing action, and wherein said predetermined release of active ingredient is suitable for twice daily administration, wherein said soluble polymer(s) is (are) selected from the group consisting of: polyvinyl alcohols, water soluble alkyl celluloses, hydroxyalkyl celluloses, water soluble cellulose esters, polyalkylene glycols, polyvinylpyrrolidone, and polymers thereof, and said water insoluble polymer(s) is (are) selected from the group consisting of water insoluble alkyl celluloses, water insoluble cellulose esters, nitro celluloses, polymers of acrylic and methacrylic acids and esters thereof, polyamide, polycarbonates, polyalkylenes, polyalkyline oxides, polyalkylene terephthalates, polyvinyl ethers, polyvinyl esters, polyvinyl halides, polyglycolides, polysiloxanes, polyurethanes, and co-polymers thereof.

3. A pharmaceutical composition containing a pharmaceutically effective amount of a controlled release powder according to claim 2.

4. A pharmaceutical composition containing a pharmaceutically effective amount of a controlled release powder according to claim 2 and which is in the form of tablets, capsules, suppositories, implants, or ocular inserts.

5. A pharmaceutical composition according to claim 3 which is the form of chewable tablets or melt tablets.

6. A pharmaceutical composition containing a pharmaceutically effective amount of a controlled release powder according to claim 2 and which is in the form of a liquid for oral administration.

7. A pharmaceutical composition according to claim 6 which is in the form of drops, a suspension, a syrup, or an infusion or solution.

* * * * *

UNITED STATES PATENT AND TRADEMARK OFFICE
CERTIFICATE OF CORRECTION

PATENT NO. : 4,940,588
DATED : July 10, 1990
INVENTOR(S) : Sparks et al.

It is certified that error appears in the above-identified patent and that said Letters Patent is hereby corrected as shown below:

Under the subheading "[56] References Cited" on the captioned page of the Patent with the Patent Number, correct the data for the following entries as follows:

3,943,063   3/1976   Morishita et al. ............ 252/316

4,384,975   5/1983   Fong ....................... 427/213

4,389,330   6/1983   Tice et al. ................ 427/213

There are dual references to Banker et al, U.S. Patent No. 3,629,392 with different subclasses, and Won, U.S. Patent 4,690,825. (2nd occurrence) references in each case should be eliminated or the subclasses combined.

Under the subheading "FOREIGN PATENT DOCUMENTS", the following references to foreign patent publications should be corrected:

0002574A1   1/1978   European Pat. Off.

2059764A    9/1980   United Kingdom

Correct the stenographical error in the following entry:

2147501A   9/1985   United Kingdom, should be 9/1984.
--2147501A   9/1984   United Kingdom--.

UNITED STATES PATENT AND TRADEMARK OFFICE
CERTIFICATE OF CORRECTION

PATENT NO. : 4,940,588
DATED : July 10, 1990
INVENTOR(S) : Sparks et al.

It is certified that error appears in the above-identified patent and that said Letters Patent is hereby corrected as shown below:

Under the same subheading "FOREIGN PATENT DOCUMENTS", list the following foreign patent documents:

"KT3010 Australia" ...

"N39886 Great Britain" ...

"2447 Canada" ...

"678097 2/1966 Belgium" ...

"WC7800011 12/1978 PCT" ...

"2237503 10/1974 Germany" ...

"1974-93522 9/1974 Japan" ...

"5094112 7/1975 Japan" ...

"56152739 11/1981 Japan" ...

"5524938 4/1977 Japan" ...

"58401 1/1976 Japan" ...

"4962623 6/1974 Japan".

In column 1, line 6, under the subheading "RELATED APPLICATIONS", capitalize "Application" and "Continuation", place a comma after "Ser. No. 792,801", and on the following line 7, place a comma after "10.30.85", and a period after "abandoned".

UNITED STATES PATENT AND TRADEMARK OFFICE
CERTIFICATE OF CORRECTION

PATENT NO. : 4,940,588

DATED : July 10, 1990

INVENTOR(S) : Sparks et al.

It is certified that error appears in the above-identified patent and that said Letters Patent is hereby corrected as shown below:

In column 1, line 35, underline _in vivo_.

In column 5, line 42, correct the spelling of "potassium".

In column 9, line 43, correct the equation as follows:

$$D \sim \sqrt{t}$$

In column 10, line 30, correct the spelling of "homogenizer".

In column 10, line 67, correct the spelling of "normally".

Rewrite the titles of all examples _not_ in all caps and underline each (Examples 1-8, 10-12, 15, and 19-22). Accordingly: underline each of the following titles:

| Example | Title | Location |
|---|---|---|
| 1 | Preparation of micro-particles containing theophylline | col. 10, l. 8 |
| 2 | Preparation of micro-particles containing acetaminophen | col. 11, l. 3 and l. 4 |

UNITED STATES PATENT AND TRADEMARK OFFICE
CERTIFICATE OF CORRECTION

PATENT NO. : 4,940,588
DATED : July 10, 1990
INVENTOR(S) : Sparks et al.

It is certified that error appears in the above-identified patent and that said Letters Patent is hereby corrected as shown below:

| Example | Title | Location |
|---|---|---|
| 3 | Preparation of micro-particles containing nifedipine | col. 11, l. 29 |
| 4 | Preparation of micro-particles containing dextromethorphan hydrobromide | col. 11, l. 52 and l. 53 |
| 5 | Preparation of micro-particles containing saccharin sodium | col. 12, l. 2 and l. 3 |
| 6 | Preparation of micro-particles containing pseudoephedrine hydrochloride | col. 12, l. 27 and l. 28 |
| 7 | Preparation of micro-particles containing carbinoxamine maleate | col. 12, l. 51 and l. 52 |
| 8 | Preparation of micro-particles containing guaiphenesin | col. 13, l. 3 |
| 10 | Preparation of micro-particles containing erythromycin base | col. 13, l. 42 and 43 |
| 11 | Preparation of theophylline syrup | col. 14, l. 17 |
| 12 | Theophylline suspension | col. 15, l. 21 |
| 15 | Acetaminophen suspension | col. 17, l. 41 |

UNITED STATES PATENT AND TRADEMARK OFFICE
CERTIFICATE OF CORRECTION

PATENT NO. : 4,940,588

DATED : July 10, 1990

INVENTOR(S) : Sparks et al.

It is certified that error appears in the above-identified patent and that said Letters Patent is hereby corrected as shown below:

| Example | Title | Location |
|---|---|---|
| 19 | Chewable Tablet containing acetaminophen | col. 20, l. 9 |
| 20 | "Melt" tablets containing acetaminophen | col. 20, l. 41 |
| 21 | Capsules containing nifedipine | col. 21, l. 12 |
| 22 | Non-aqueous suspension of potassium chloride | col. 21, l. 35 |

In Example 16, line 52, under column 3 under the subheading of "Table 8" entitled "Suspension of Example 16", correct the entry from "14.43" to -- 14.34 --.

In column 19, Example 17, line 23, correct the entry in the second column under the subheading "Tylenol Elixir" in Table 9 from "4.5" to -- 4.35 --.

In column 21, line 55, replace "at" with -- a --.

In column 22, line 59, in Claim 2, change "amide" to -- amides --.

UNITED STATES PATENT AND TRADEMARK OFFICE
CERTIFICATE OF CORRECTION

PATENT NO. : 4,940,588

DATED : July 10, 1990

INVENTOR(S) : Sparks et al.

It is certified that error appears in the above-identified patent and that said Letters Patent is hereby corrected as shown below:

In column 22, line 59, in Claim 2, change "amide" to -- amides --.

Signed and Sealed this

First Day of October, 1991

Attest:

Attesting Officer

HARRY F. MANBECK, JR.

Commissioner of Patents and Trademarks